United States Patent
Hudecek et al.

(10) Patent No.: US 11,149,073 B2
(45) Date of Patent: Oct. 19, 2021

(54) ROR1-SPECIFIC CHIMERIC ANTIGEN RECEPTORS (CAR) WITH HUMANIZED TARGETING DOMAINS

(71) Applicant: JULIUS-MAXIMILIANS-UNIVERSITÄT WÜRZBURG, Würzburg (DE)

(72) Inventors: Michael Hudecek, Höchberg (DE); Andreas Mades, Wiesbaden Biebrich (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 0 days.

(21) Appl. No.: 16/607,069

(22) PCT Filed: Apr. 27, 2018

(86) PCT No.: PCT/EP2018/060887
§ 371 (c)(1),
(2) Date: Oct. 21, 2019

(87) PCT Pub. No.: WO2018/197675
PCT Pub. Date: Nov. 1, 2018

(65) Prior Publication Data
US 2020/0040058 A1 Feb. 6, 2020

(30) Foreign Application Priority Data

Apr. 28, 2017 (EP) .................................. 17168805

(51) Int. Cl.
| | | |
|---|---|---|
| *C07K 14/725* | (2006.01) | |
| *A61P 35/00* | (2006.01) | |
| *A61K 35/17* | (2015.01) | |
| *C07K 14/705* | (2006.01) | |
| *C07K 16/28* | (2006.01) | |
| *C12N 5/0783* | (2010.01) | |
| *C12N 15/86* | (2006.01) | |

(52) U.S. Cl.
CPC .......... *C07K 14/7051* (2013.01); *A61K 35/17* (2013.01); *A61P 35/00* (2018.01); *C07K 14/70517* (2013.01); *C07K 14/70521* (2013.01); *C07K 14/70578* (2013.01); *C07K 16/2803* (2013.01); *C12N 5/0636* (2013.01); *C12N 15/86* (2013.01); *C07K 2317/24* (2013.01); *C07K 2319/03* (2013.01); *C12N 2740/15043* (2013.01)

(58) Field of Classification Search
None
See application file for complete search history.

(56) References Cited

U.S. PATENT DOCUMENTS

| | | |
|---|---|---|
| 2016/0158359 A1 | 6/2016 | Gilbert |
| 2016/0333114 A1 | 11/2016 | Williams et al. |

FOREIGN PATENT DOCUMENTS

| | | |
|---|---|---|
| WO | WO 2010/124188 A1 | 10/2010 |
| WO | WO 2012/075158 A1 | 6/2012 |
| WO | WO 2014/126884 A1 | 8/2014 |
| WO | WO 2015/066551 A2 | 5/2015 |
| WO | WO 2016/016344 A1 | 2/2016 |
| WO | WO 2016/090369 A1 | 6/2016 |
| WO | WO 2016/094873 A2 | 6/2016 |
| WO | WO 2016/115559 A1 | 7/2016 |
| WO | WO 2016/164731 A2 | 10/2016 |
| WO | WO 2016/176652 A2 | 11/2016 |
| WO | WO 2016/187216 A1 | 11/2016 |
| WO | WO 2017/070649 A1 | 4/2017 |
| WO | WO 2017/072361 A1 | 5/2017 |
| WO | WO 2017/127664 A1 | 7/2017 |

OTHER PUBLICATIONS

Li et al (Proc. Natl. Acad. Sci. USA 77:3211-3214, 1980) (Year: 1980).*
Lederman et al (Molecular Immunology 28:1171-1181, 1991) (Year: 1991).*
Kalos, M., et al., T cells with chimeric antigen receptors have potent antitumor effects and can establish memory in patients with advanced leukemia. Sci Transl Med, 2011, 3(95): p. 95ra73.
Kochenderfer, J.N., et al., B-cell depletion and remissions of malignancy along with cytokine-associated toxicity in a clinical trial of anti-CD19 chimeric-antigen-receptor-transduced T cells. Blood, 2012, 119(12): p. 2709-20.
Kochenderfer, J.N., et al., Eradication of B-lineage cells and regression of lymphoma in a patient treated with autologous T cells genetically engineered to recognize CD19. Blood, 2010, 116(20): p. 4099-102.
Morgan, R.A., et al., Cancer regression in patients after transfer of genetically engineered lymphocytes. Science, 2006, 314(5796): p. 126-9.
Porter, D.L., et al., Chimeric antigen receptor-modified T cells in chronic lymphoid leukemia. N Engl J Med, 2011, 365(8): p. 725-33.
Eshhar, Z., et al., Specific activation and targeting of cytotoxic lymphocytes through chimeric single chains consisting of antibody-binding domains and the gamma or zeta subunits of the immunoglobulin and T-cell receptors. Proc Natl Acad Sci U S A, 1993, 90(2): p. 720-4.

(Continued)

*Primary Examiner* — Padmavathi Baskar
(74) *Attorney, Agent, or Firm* — James S. Keddie; Bozicevic, Field & Francis LLP

(57) ABSTRACT

The invention relates to chimeric antigen receptors (CAR) with a humanized targeting domain specific to the antigen ROR1. The invention encompasses the polynucleotides, vectors encoding said CARs and the isolated cells expressing them at their surface, in particularly for their use in immunotherapy.

14 Claims, 19 Drawing Sheets
Specification includes a Sequence Listing.

(56) References Cited

OTHER PUBLICATIONS

Kershaw, M.H., et al., Supernatural T cells: genetic modification of T cells for cancer therapy. Nat Rev Immunol, 2002, 5(12): p. 928-40.
Sadelain, M., I. Riviere, and R. Brentjens, Targeting tumours with genetically enhanced T lymphocytes. Nat Rev Cancer, 2003, 3(1): p. 35-45.
Brentjens, R.J., et al., Safety and persistence of adoptively transferred autologous CD19-targeted T cells in patients with relapsed or chemotherapy refractory B-cell leukemias. Blood, 2011, 118(18): p. 4817-28.
Hudecek, M., et al., the B-cell tumor-associated antigen ROR1 can be targeted with T cells modified to express a ROR1-specific chimeric antigen receptor Blood, 2010, 116(22): p. 4532-41.
Matsuda, T., et al., Expression of the receptor tyrosine kinase genes, Ror1 and Ror2, during mouse development. Mech Dev, 2001, 105(1-2): p. 153-6.
Rosenwald, A., et al., Relation of gene expression phenotype to immunoglobulin mutation genotype in B cell chronic lymphocytic leukemia. J Exp Med, 2001, 194(11): p. 1639-47.
Klein, U., et al., Gene expression profiling of B cell chronic lymphocytic leukemia reveals a homogeneous phenotype related to memory B cells. J Exp Med, 2001, 194(11): p. 1625-38.
Baskar, S., et al., Unique cell surface expression of receptor tyrosine kinase ROR1 in human B-cell chronic lymphocytic leukemia. Clin Cancer Res, 2008, 14(2): p. 396-404.
Bicocca, V.I., et al., Crosstalk between ROR1 and the Pre-B cell receptor promotes survival of t(1;19) acute lymphoblastic leukemia. Cancer Cell, 2012, 22(5): p. 656-67.
Daneshmanesh, A.H., et al., Ror1, a cell surface receptor tyrosine kinase is expressed in chronic lymphocytic leukemia and may serve as a putative target for therapy. Int J Cancer, 2008, 123(5): p. 1190-5.
Fukuda, T., et al., Antisera induced by infusions of autologous Ad-CD154-leukemia B cells identify ROR1 as an oncofetal antigen and receptor for Wnt5a. Proc Natl Aced Sci U S A, 2008, 105(8): p. 3047-52.
Yamaguchi, T., et al., NKX2-1/TITF1/TTF-1-Induced ROR1 is required to sustain EGFR survival signaling in lung adenocarcinoma. Cancer Cell, 2012, 21(3): p. 348-61.
Zhang, S., et al., ROR1 is expressed in human breast cancer and associated with enhanced tumor-cell growth. PLoS One, 2012, 7(3): p. e31127.
Zhang, S., et al., The onco-embryonic antigen ROR1 is expressed by a variety of human cancers. Am J Pathol, 2012, 181(6): p. 1903-10.
Dave, H., et al., Restricted cell surface expression of receptor tyrosine kinase ROR1 in pediatric B-lineage acute lymphoblastic leukemia suggests targetability with therapeutic monoclonal antibodies. PLoS One, 2012, 7(12): p. e52655.
Gentile, A., et al., Ror1 is a pseudokinase that is crucial for Met-driven tumorigenesis. Cancer Res, 2011, 71(8): p. 3132-41.
Choudhury, A., et al., Silencing of ROR1 and FMOD with siRNA results in apoptosis of CLL cells. Br J Haematol, 2010, 151(4): p. 327-35.
Maude, S.L., et al., Chimeric antigen receptor T cells for sustained remissions in leukemia. N Engl J Med, 2014, 371(16): p. 1507-17.
Grupp, S.A., et al., Chimeric antigen receptor-modified T cells for acute lymphoid leukemia. N Engl J Med, 2013, 368(16): p. 1509-18.
Davila, M.L., et al., Efficacy and toxicity management of 19-28z CAR T cell therapy in B cell acute lymphoblastic leukemia. Sci Transl. Med, 2014, 6(224): p. 224ra25.
Lamers, C.H., et al., Treatment of metastatic renal cell carcinoma with CAIX CAR-engineered T cells: clinical evaluation and management of on-target toxicity. Mol Ther, 2013, 21(4): p. 904-12.
Turtle, C.J., et al., CD19 CAR-T cells of defined CD4+:CD8+ composition in adult B cell ALL patients. J Clin Invest, 2016, 126(6): p. 2123-38.
Maus, M.V., et al., T cells expressing chimeric antigen receptors can cause anaphylaxis in humans. Cancer Immunol Res, 2013, 1(1): p. 26-31.
Sommermeyer, D., et al., Fully human CD19-specific chimeric antigen receptors for T-cell therapy. Leukemia, 2017, 31(10): 2191-2199.
Waldmeier, L., et al., Transpo-mAb display: Transposition-mediated B cell display and functional screening of full-length IgG antibody libraries. MAbs, 2016, 8(4): p. 726-40.
Baca, M., et al., Antibody humanization using monovalent phage display. J Biol Chem, 1997, 272(16): p. 10678-84.
Altschul, S.F., et al., Basic local alignment search tool. J Mol Biol, 1990, 215(3): p. 403-10.
Altschul, S.F., et al., Gapped BLAST and PSI-BLAST: a new generation of protein database search programs. Nucleic Acids Res, 1997, 25(17): p. 3389-402.
Wang, X., et al., A transgene-encoded cell surface polypeptide for selection, in vivo tracking, and ablation of engineered cells. Blood, 2011, 118(5): p. 1255-63.
Yang, J. et al., Therapeutic potential and challenges of targeting receptor tyrosine kinase ROR1 with monoclonal antibodies in B-cell malignancies. PLoS One. 2011, 6(6):e21018.
Gardner et al., T Cell Products of Defined CD4:CD8 Composition and Prescribed Levels of CD19CAR/Egfrt Transgene Expression Mediate Regression of Acute Lymphoblastic Leukemia in the Setting of Post-Allohsct Relapse. Blood. 2014, 124:3711.
Berger et al., "Safety of Targeting ROR1 in Primates with Chimeric Antigen Receptor-Modified T Cells", Cancer Immunology Research, 2014, 3(2): 206-216.
Gohil et al., "Novel Mumanised ROR1 Chimeric Antigen Receptors for the Treatment of Haematological Malignancies", Blood, 2016, 128(22): 3361.
Hudecek et al., "Receptor Affinity and Extracellular Domain Modifications Affect Tumor Recognition by ROR1-Specific Chimeric Antigen Receptor T Cells", Clinical Cancer Research, 2013, 19(12): 3153-3164.
Hudecek et al., "The Nonsignaling Extracellular Spacer Domain of Chimeric Antigen Receptors Is Decisive for In Vivo Antitumor Activity", Cancer Immunology Research, 3(2), 2014, 125-135.

\* cited by examiner

FIG. 1A

>h2A2 VH sequence (SEQ ID No: 1)
EVQLVQSGAEVKKPGASVKVSCKASGYTFSDYEMHWVRQAPGQGLEWLGAIDPETGG
TAYNQKFKGRVTMTGDTSISTAYMELSRLTSDDTAVYYCTGYDYDSFTYWGQGTLV
SVSS >h2A2 VL sequence (SEQ ID No: 2)
DIQMTQSPSSLSTSVGDRVTITCKASQNVDAAVAWYQQKPGKAPKLLIYSASNRYTG
VASRFSGSGSGTDFTFTISSLQSEDLADYFCQQYDIYPYTFGQGTKLEIK

FIG. 1B

| | |
|---|---|
| GMCSF signal peptide | MLLLVTSLLLCELPHPAFLLIP (SEQ ID No: 7) |
| h2A2 heavy chain variable domain (VH) | EVQLVQSGAEVKKPGASVKVSCKASGYTFSDYEMHWVRQAPGQGLEWLGAIDPETGGTAYN QKFKGRVTMTGDTSISTAYMELSRLTSDDTAVYYCTGYYDYDSFTYWGQGTLVSVSS (SEQ ID No: 1) |
| 4(GS)x3 linker | GGGGSGGGGSGGGGS (SEQ ID No: 8) |
| h2A2 light chain variable domain (VL) | DIQMTQSPSSLSTSVGDRVTITCKASQNVDAAVAWYQQKPGKAPKLLIYSASNRYTGVASR FSGSGSGTDFTFTISSLQSEDLADYFCQQYDIYPYTFGQGTKLEIK (SEQ ID No: 2) |
| IgG4 hinge domain | ESKYGPPCPPCP (SEQ ID No: 9) |
| CD28 transmembrane domain | MFWVLVVVGGVLACYSLLVTVAFIIFWV (SEQ ID No: 11) |
| 4-1BB costimulatory domain | KRGRKKLLYIFKQPFMRPVQTTQEEDGCSCRFPEEEEGGCEL (SEQ ID No: 12) |
| CD3z signaling domain | RVKFSRSADAPAYQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPPR (SEQ ID No: 13) |
| T2A ribosomal skipping sequence | LEGGGEGRGSLLTCGDVEENPGPR (SEQ ID No: 14) |
| GMCSF signal peptide | MLLLVTSLLLCELPHPAFLLIP (SEQ ID No: 7) |
| EGFRt | RKVCNGIGIGEFKDSLSINATNIKHFKNCTSISGDLHILPVAFRGDSFTHTPPLDPQELDI LKTVKEITGFLLIQAWPENRTDLHAFENLEIIRGRTKQHGQFSLAVVSLNITSLGLRSLKE ISDGDVIISGNKNLCYANTINWKKLFGTSGQKTKIISNRGENSCKATGQVCHALCSPEGCW GPEPRDCVSCRNVSRGRECVDKCNLLEGEPREFVENSECIQCHPECLPQAMNITCTGRGPD NCIQCAHYIDGPHCVKTCPAGVMGENNTLVWKYADAGHVCHLCHPNCTYGCTGPGLEGCPT NGPKIPSIATGMVGALLLLLVVALGIGLFM* (SEQ ID No: 15) |

FIG. 2A

>hR11 VH sequence (SEQ ID No: 3)
EVQLVQSGGGLVQPGGSLRLSCAASGSDINDYPISWVRQAPGKGLEWVSFINSGGSTWYA
SWVKGRFTISRDNAKNSLYLQMNSLRDDDTATYFCARGYSTYYGDFNIWGQGTLVTVSS >hR11 VL sequence (SEQ ID No: 4)
DIVMTQSPSSLSASVGDRVTITCQASQSIDSNLAWFQQKPGKAPKSLIYRASNLASGVPS
KFSGSGSGTDFTLTISSLQREDAATYYCLGGVGNVSYRTSFGGGTKVEIK

FIG. 2B

| | |
|---|---|
| GMCSF signal peptide | MLLLVTSLLLCELPHPAFLLIP (SEQ ID No: 7) |
| hR11 heavy chain variable domain (VH) | EVQLVQSGGGLVQPGGSLRLSCAASGSDINDYPISWVRQAPGKGLEWVSFINSGGSTWYAS WVKGRFTISRDNAKNSLYLQMNSLRDDDTATYFCARGYSTYYGDFNIWGQGTLVTVSS (SEQ ID No: 3) |
| 4(GS)x3 linker | GGGGSGGGGSGGGGS (SEQ ID No: 8) |
| hR11 light chain variable domain (VL) | DIVMTQSPSSLSASVGDRVTITCQASQSIDSNLAWFQQKPGKAPKSLIYRASNLASGVPSK FSGSGSGTDFTLTISSLQREDAATYCLGGVGNVSYRTSFGGGTKVEIK (SEQ ID No: 4) |
| IgG4 CH2CH3 4/2NQ | ESKYGPPCPPCPAPPVAGPSVFLFPPKPKDTLMISRTPEVTCVVVDVSQEDPEVQFNWYVD GVEVHNAKTKPREEQFQSTYRVVSVLTVLHQDWLNGKEYKCKVSNKGLPSSIEKTISKAKG QPREPQVYTLPPSQEEMTKNQVSLTCLVKGFYPSDIAVEWESNGQPENNYKTTPPVLDSDG SFFLYSRLTVDKSRWQEGNVFSCSVMHEALHNHYTQKSLSLSLGK (SEQ ID No: 10) |
| CD28 transmembrane domain | MFWVLVVVGGVLACYSLLVTVAFIIFWV (SEQ ID No: 11) |
| 4-1BB costimulatory domain | KRGRKKLLYIFKQPFMRPVQTTQEEDGCSCRFPEEEEGGCEL (SEQ ID No: 12) |
| CD3z signaling domain | RVKFSRSADAPAYQQGQNQLYNELNLGRREEYDVLDKRRGRDPEMGGKPRRKNPQEGLYNE LQKDKMAEAYSEIGMKGERRRGKGHDGLYQGLSTATKDTYDALHMQALPPR (SEQ ID No: 13) |
| T2A ribosomal skipping sequence | LEGGGEGRGSLLTCGDVEENPGPR (SEQ ID No: 14) |
| GMCSF signal peptide | MLLLVTSLLLCELPHPAFLLIP (SEQ ID No: 7) |
| EGRFt | RKVCNGIGIGEFKDSLSINATNIKHFKNCTSISGDLHILPVAFRGDSFTHTPLDPQELDI LKTVKEITGFLLIQAWPENRTDLHAFENLEIIRGRTKQHGQFSLAVVSLNITSLGLRSLKE ISDGDVIISGNKNLCYANTINWKKLFGTSGQKTKIISNRGENSCKATGQVCHALCSPEGCW GPEPRDCVSCRNVSRGRECVDKCNLLEGEPREFVENSECIQCHPECLPQAMNITCTGRGPD NCIQCAHYIDGPHCVKTCPAGVMGENNTLVWKYADAGHVCHLCHPNCTYGCTGPGLEGCPT NGPKIPSIATGMVGALLLLLVVALGIGLFM* (SEQ ID No: 15) |

FIG. 3A

>hR12 VH sequence (SEQ ID No: 5)
QVQLVESGGALVQPGGSLTLSCKASGFDFSAYYMSWVRQAPGKGLEWIATIYPSSGKTYYAA
SVQGRFTISADNAKNTVYLQMNSLTAADTATYFCARDSYADDGALFNIWGQGTLVTVSS >hR12 VL sequence (SEQ ID No: 6)
QLVLTQSPSVSAALGSSAKITCTLSSAHKTDTIDWYQQLAGQAPRYLMYVQSDGSYEKRSGV
PDRFSGSSSSGADRYLIISSVQADDEADYYCGADYIGGYVFGGGTQLTVG

FIG. 3B

| | |
|---|---|
| GMCSF signal peptide | MLLLVTSLLLCELPHPAFLLIP (SEQ ID No: 7) |
| hR12 heavy chain variable domain (VH) | QVQLVESGGALVQPGGSLTLSCKASGFDFSAYYMSWVRQAPGKGLEWIATIYPSSGKTYYAAS VQGRFTISADNAKNTVYLQMNSLTAADTATYFCARDSYADDGALFNIWGQGTLVTVSS (SEQ ID No: 5) |
| 4(GS)x3 linker | GGGGSGGGGSGGGGS (SEQ ID No: 8) |
| hR12 light chain variable domain (VL) | QLVLTQSPSVSAALGSSAKITCTLSSAHKTDTIDWYQQLAGQAPRYLMYVQSDGSYEKRSGVP DRFSGSSSGADRYLIISSVQADDEADYYCGADYIGGYVFGGGTQLTVG (SEQ ID No: 6) |
| IgG4 hinge domain | ESKYGPPCPPCP (SEQ ID No: 9) |
| CD28 transmembrane domain | MFWVLVVVGGVLACYSLLVTVAFIIFWV (SEQ ID No: 10) |
| 4-1BB costimulatory domain | KRGRKKLLYIFKQPFMRPVQTTQEEDGCSRFPEEEEGGCEL (SEQ ID No: 12) |
| CD3z signaling domain | RVKFSRSADAPAYQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR (SEQ ID No: 13) |
| T2A ribosomal skipping sequence | LEGGGEGRGSLLTCGDVEENPGPR (SEQ ID No: 14) |
| GMCSF signal peptide | MLLLVTSLLLCELPHPAFLLIP (SEQ ID No: 7) |
| EGFRt | RKVCNGIGIGEFKDSLSINATNIKHFKNCTSISGDLHILPVAFRGDSFTHTPPLDPQELDILK TVKEITGFLLIQAWPENRTDLHAFENLEIIRGRTKQHGQFSLAVVSLNITSLGLRSLKEISDG DVIISGNKNLCYANTINWKKLFGTSGQKTKIISNRGENSCKATGQVCHALCSPEGCWGPEPRD CVSCRNVSRGRECVDKCNLLEGEPREFVENSECIQCHPECLPQAMNITCTGRGPDNCIQCAHY IDGPHCVKTCPAGVMGENNTLVWKYADAGHVCHLCHPNCTYGCTGPGLEGCPTNGPKIPSIAT GMVGALLLLVALGIGLFM* (SEQ ID No: 15) |

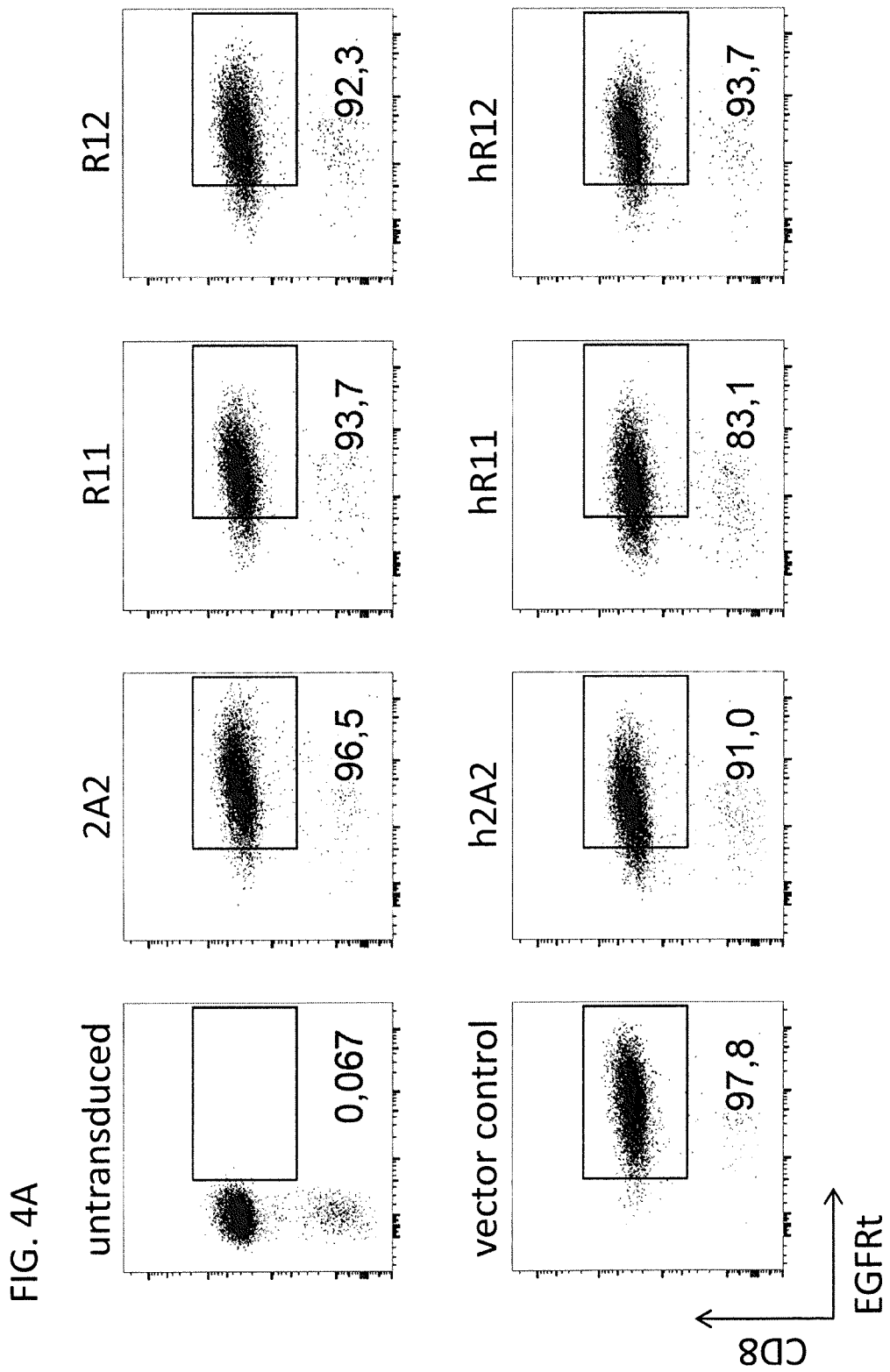

FIG. 7C

| CAR T cells | Target cells | Number of cell divisions | | | | | |
|---|---|---|---|---|---|---|---|
| | | 0 | 1 | 2 | 3 | 4 | 5 |
| EGFRt | K562 | 95 | 4 | 0 | 0 | 0 | 0 |
| 2A2 | K562 | 92 | 6 | 1 | 0 | 0 | 0 |
| h2A2 | K562 | 95 | 4 | 1 | 0 | 0 | 0 |
| R11 | K562 | 90 | 9 | 1 | 0 | 0 | 0 |
| hR11 | K562 | 92 | 6 | 1 | 1 | 0 | 0 |
| R12 | K562 | 95 | 4 | 1 | 0 | 0 | 0 |
| hR12 | K562 | 97 | 2 | 0 | 0 | 0 | 0 |
| EGFRt | K562-ROR1 | 95 | 4 | 1 | 0 | 0 | 0 |
| 2A2 | K562-ROR1 | 30 | 32 | 21 | 13 | 4 | 1 |
| h2A2 | K562-ROR1 | 5 | 16 | 28 | 36 | 12 | 3 |
| R11 | K562-ROR1 | 7 | 12 | 22 | 36 | 18 | 6 |
| hR11 | K562-ROR1 | 47 | 45 | 6 | 1 | 0 | 0 |
| R12 | K562-ROR1 | 8 | 21 | 33 | 31 | 6 | 1 |
| hR12 | K562-ROR1 | 7 | 23 | 33 | 30 | 6 | 1 |
| EGFRt | MDA-MB-231 | 58 | 33 | 7 | 2 | 0 | 0 |
| 2A2 | MDA-MB-231 | 21 | 34 | 25 | 15 | 4 | 1 |
| h2A2 | MDA-MB-231 | 9 | 10 | 21 | 41 | 15 | 4 |
| R11 | MDA-MB-231 | 12 | 12 | 21 | 35 | 16 | 5 |
| hR11 | MDA-MB-231 | 21 | 45 | 22 | 9 | 2 | 2 |
| R12 | MDA-MB-231 | 43 | 14 | 23 | 16 | 3 | 1 |
| hR12 | MDA-MB-231 | 16 | 16 | 30 | 30 | 6 | 1 |
| EGFRt | A549 | 93 | 6 | 1 | 0 | 0 | 0 |
| 2A2 | A549 | 59 | 25 | 10 | 4 | 1 | 0 |
| h2A2 | A549 | 24 | 34 | 25 | 14 | 3 | 1 |
| R11 | A549 | 73 | 18 | 6 | 3 | 0 | 0 |
| hR11 | A549 | 51 | 40 | 7 | 2 | 0 | 0 |
| R12 | A549 | 18 | 31 | 27 | 19 | 5 | 1 |
| hR12 | A549 | 33 | 34 | 20 | 11 | 2 | 0 |

SEQUENCE LISTING

<160> NUMBER OF SEQ ID NOS: 24

<210> SEQ ID NO 1
<211> LENGTH: 118
<212> TYPE: PRT
<213> ORGANISM: Artificial Sequence
<220> FEATURE:
<223> OTHER INFORMATION: h2A2 VH sequence

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Glu Met His Trp Val Arg Gln Ala Pro Gly Gln Gly Leu Glu Trp Leu
            35                  40                  45

Gly Ala Ile Asp Pro Glu Thr Gly Gly Thr Ala Tyr Asn Gln Lys Phe
        50                  55                  60

Lys Gly Arg Val Thr Met Thr Gly Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Thr Gly Tyr Tyr Asp Tyr Asp Ser Phe Thr Tyr Trp Gly Gln Gly Thr
                100                 105                 110

Leu Val Ser Val Ser Ser
            115

<210> SEQ ID NO 2
<211> LENGTH: 107
<212> TYPE: PRT
<213> ORGANISM: Artificial Sequence
<220> FEATURE:
<223> OTHER INFORMATION: h2A2 VL sequence

<400> SEQUENCE: 2

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asn Val Asp Ala Ala
                20                  25                  30

Val Ala Trp Tyr Gln Gln Lys Pro Gly Lys Ala Pro Lys Leu Leu Ile
            35                  40                  45

Tyr Ser Ala Ser Asn Arg Tyr Thr Gly Val Ala Ser Arg Phe Ser Gly
        50                  55                  60

Ser Gly Ser Gly Thr Asp Phe Thr Phe Thr Ile Ser Ser Leu Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gln Gly Thr Lys Leu Glu Ile Lys
                100                 105

<210> SEQ ID NO 3
<211> LENGTH: 119
<212> TYPE: PRT
<213> ORGANISM: Artificial Sequence
<220> FEATURE:
<223> OTHER INFORMATION: hR11 VH sequence

<400> SEQUENCE: 3

Glu Val Gln Leu Val Gln Ser Gly Gly Gly Leu Val Gln Pro Gly Gly
1               5                   10                  15

-continued

Ser Leu Arg Leu Ser Cys Ala Ala Ser Gly Ser Asp Ile Asn Asp Tyr
            20                  25                  30

Pro Ile Ser Trp Val Arg Gln Ala Pro Gly Lys Gly Leu Glu Trp Val
        35                  40                  45

Ser Phe Ile Asn Ser Gly Gly Ser Thr Trp Tyr Ala Ser Trp Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Asp Asp Thr Ala Thr Tyr Phe Cys Ala
                85                  90                  95

Arg Gly Tyr Ser Thr Tyr Tyr Gly Asp Phe Asn Ile Trp Gly Gln Gly
            100                 105                 110

Thr Leu Val Thr Val Ser Ser
            115

<210> SEQ ID NO 4
<211> LENGTH: 110
<212> TYPE: PRT
<213> ORGANISM: Artificial Sequence
<220> FEATURE:
<223> OTHER INFORMATION: hR11 VL sequence

<400> SEQUENCE: 4

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Asp Ser Asn
            20                  25                  30

Leu Ala Trp Phe Gln Gln Lys Pro Gly Lys Ala Pro Lys Ser Leu Ile
        35                  40                  45

Tyr Arg Ala Ser Asn Leu Ala Ser Gly Val Pro Ser Lys Phe Ser Gly
    50                  55                  60

Ser Gly Ser Gly Thr Asp Phe Thr Leu Thr Ile Ser Ser Leu Gln Arg
65                  70                  75                  80

Glu Asp Ala Ala Thr Tyr Tyr Cys Leu Gly Gly Val Gly Asn Val Ser
                85                  90                  95

Tyr Arg Thr Ser Phe Gly Gly Gly Thr Lys Val Glu Ile Lys
            100                 105                 110

<210> SEQ ID NO 5
<211> LENGTH: 121
<212> TYPE: PRT
<213> ORGANISM: Artificial Sequence
<220> FEATURE:
<223> OTHER INFORMATION: hR12 VH sequence

<400> SEQUENCE: 5

Gln Val Gln Leu Val Glu Ser Gly Gly Ala Leu Val Gln Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Ala Ser Val
    50                  55                  60

Gln Gly Arg Phe Thr Ile Ser Ala Asp Asn Ala Lys Asn Thr Val Tyr
65                  70                  75                  80

Leu Gln Met Asn Ser Leu Thr Ala Ala Asp Thr Ala Thr Tyr Phe Cys

```
                    85                  90                  95

Ala Arg Asp Ser Tyr Ala Asp Asp Gly Ala Leu Phe Asn Ile Trp Gly
            100                 105                 110

Gln Gly Thr Leu Val Thr Val Ser Ser
        115                 120

<210> SEQ ID NO 6
<211> LENGTH: 111
<212> TYPE: PRT
<213> ORGANISM: Artificial Sequence
<220> FEATURE:
<223> OTHER INFORMATION: hR12 VL sequence

<400> SEQUENCE: 6

Gln Leu Val Leu Thr Gln Ser Pro Ser Val Ser Ala Ala Leu Gly Ser
1               5                   10                  15

Ser Ala Lys Ile Thr Cys Thr Leu Ser Ser Ala His Lys Thr Asp Thr
                20                  25                  30

Ile Asp Trp Tyr Gln Gln Leu Ala Gly Gln Ala Pro Arg Tyr Leu Met
            35                  40                  45

Tyr Val Gln Ser Asp Gly Ser Tyr Glu Lys Arg Ser Gly Val Pro Asp
        50                  55                  60

Arg Phe Ser Gly Ser Ser Gly Ala Asp Arg Tyr Leu Ile Ile Ser
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Gly
            100                 105                 110

<210> SEQ ID NO 7
<211> LENGTH: 22
<212> TYPE: PRT
<213> ORGANISM: Artificial Sequence
<220> FEATURE:
<223> OTHER INFORMATION: GMCSF signal peptide

<400> SEQUENCE: 7

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 8
<211> LENGTH: 15
<212> TYPE: PRT
<213> ORGANISM: Artificial Sequence
<220> FEATURE:
<223> OTHER INFORMATION: 4(GS)x3 linker

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: IgG4 hinge domain

<400> SEQUENCE: 9

Glu Ser Lys Tyr Gly Pro Pro Cys Pro Pro Cys Pro
```

<210> SEQ ID NO 10
<211> LENGTH: 228
<212> TYPE: PRT
<213> ORGANISM: Artificial Sequence
<220> FEATURE:
<223> OTHER INFORMATION: IgG4 CH2CH3 4/2NQ

<400> SEQUENCE: 10

```
Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225
```

<210> SEQ ID NO 11
<211> LENGTH: 28
<212> TYPE: PRT
<213> ORGANISM: Artificial Sequence
<220> FEATURE:
<223> OTHER INFORMATION: CD28 transmembrane domain

<400> SEQUENCE: 11

```
Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25
```

<210> SEQ ID NO 12
<211> LENGTH: 42
<212> TYPE: PRT
<213> ORGANISM: Artificial Sequence
<220> FEATURE:

<223> OTHER INFORMATION: 4-1BB costimulatory domain

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Artificial Sequence
<220> FEATURE:
<223> OTHER INFORMATION: CD3z signaling domain

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 24
<212> TYPE: PRT
<213> ORGANISM: Artificial Sequence
<220> FEATURE:
<223> OTHER INFORMATION: T2A ribosomal skipping sequence

<400> SEQUENCE: 14

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 15
<211> LENGTH: 335
<212> TYPE: PRT
<213> ORGANISM: Artificial Sequence
<220> FEATURE:
<223> OTHER INFORMATION: EGFRt

<400> SEQUENCE: 15

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

-continued

```
Thr His Thr Pro Pro Leu Asp Pro Gln Glu Leu Asp Ile Leu Lys Thr
    50                  55                  60
Val Lys Glu Ile Thr Gly Phe Leu Leu Ile Gln Ala Trp Pro Glu Asn
 65                  70                  75                  80
Arg Thr Asp Leu His Ala Phe Glu Asn Leu Glu Ile Ile Arg Gly Arg
                 85                  90                  95
Thr Lys Gln His Gly Gln Phe Ser Leu Ala Val Val Ser Leu Asn Ile
            100                 105                 110
Thr Ser Leu Gly Leu Arg Ser Leu Lys Glu Ile Ser Asp Gly Asp Val
            115                 120                 125
Ile Ile Ser Gly Asn Lys Asn Leu Cys Tyr Ala Asn Thr Ile Asn Trp
130                 135                 140
Lys Lys Leu Phe Gly Thr Ser Gly Gln Lys Thr Lys Ile Ile Ser Asn
145                 150                 155                 160
Arg Gly Glu Asn Ser Cys Lys Ala Thr Gly Gln Val Cys His Ala Leu
                165                 170                 175
Cys Ser Pro Glu Gly Cys Trp Gly Pro Glu Pro Arg Asp Cys Val Ser
            180                 185                 190
Cys Arg Asn Val Ser Arg Gly Arg Glu Cys Val Asp Lys Cys Asn Leu
            195                 200                 205
Leu Glu Gly Glu Pro Arg Glu Phe Val Glu Asn Ser Glu Cys Ile Gln
210                 215                 220
Cys His Pro Glu Cys Leu Pro Gln Ala Met Asn Ile Thr Cys Thr Gly
225                 230                 235                 240
Arg Gly Pro Asp Asn Cys Ile Gln Cys Ala His Tyr Ile Asp Gly Pro
                245                 250                 255
His Cys Val Lys Thr Cys Pro Ala Gly Val Met Gly Glu Asn Asn Thr
            260                 265                 270
Leu Val Trp Lys Tyr Ala Asp Ala Gly His Val Cys His Leu Cys His
            275                 280                 285
Pro Asn Cys Thr Tyr Gly Cys Thr Gly Pro Gly Leu Glu Gly Cys Pro
290                 295                 300
Thr Asn Gly Pro Lys Ile Pro Ser Ile Ala Thr Gly Met Val Gly Ala
305                 310                 315                 320
Leu Leu Leu Leu Leu Val Val Ala Leu Gly Ile Gly Leu Phe Met
                325                 330                 335

<210> SEQ ID NO 16
<211> LENGTH: 240
<212> TYPE: PRT
<213> ORGANISM: Artificial Sequence
<220> FEATURE:
<223> OTHER INFORMATION: scFV of the non-humanized 2A2 antibody

<400> SEQUENCE: 16

Gln Val Gln Leu Gln Gln Ser Gly Ala Glu Leu Val Arg Pro Gly Ala
 1               5                  10                  15
Ser Val Thr Leu Ser Cys Lys Ala Ser Gly Tyr Thr Phe Ser Asp Tyr
             20                  25                  30
Glu Met His Trp Val Gln Thr Pro Val His Gly Leu Glu Trp Ile
             35                  40                  45
Gly Ala Ile Asp Pro Glu Thr Gly Gly Thr Ala Tyr Asn Gln Lys Phe
         50                  55                  60
Lys Gly Lys Ala Ile Leu Thr Ala Asp Lys Ser Ser Thr Ala Tyr
 65                  70                  75                  80
```

```
Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala Gly Gly Gly Gly Ser Gly Gly Gly Gly Ser
        115                 120                 125

Gly Gly Gly Gly Ser Asp Ile Val Met Thr Gln Ser Gln Lys Ile Met
    130                 135                 140

Ser Thr Thr Val Gly Asp Arg Val Ser Ile Thr Cys Lys Ala Ser Gln
145                 150                 155                 160

Asn Val Asp Ala Ala Val Ala Trp Tyr Gln Gln Lys Pro Gly Gln Ser
                165                 170                 175

Pro Lys Leu Leu Ile Tyr Ser Ala Ser Asn Arg Tyr Thr Gly Val Pro
            180                 185                 190

Asp Arg Phe Thr Gly Ser Gly Ser Gly Thr Asp Phe Thr Leu Thr Ile
        195                 200                 205

Ser Asn Met Gln Ser Glu Asp Leu Ala Asp Tyr Phe Cys Gln Gln Tyr
    210                 215                 220

Asp Ile Tyr Pro Tyr Thr Phe Gly Gly Gly Thr Lys Leu Glu Ile Lys
225                 230                 235                 240

<210> SEQ ID NO 17
<211> LENGTH: 241
<212> TYPE: PRT
<213> ORGANISM: Artificial Sequence
<220> FEATURE:
<223> OTHER INFORMATION: scFV of the non-humanized R11 antibody

<400> SEQUENCE: 17

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65                  70                  75                  80

Ser Leu Thr Thr Asp Asp Thr Ala Thr Tyr Phe Cys Ala Arg Gly Tyr
                85                  90                  95

Ser Thr Tyr Tyr Gly Asp Phe Asn Ile Trp Gly Pro Gly Thr Leu Val
            100                 105                 110

Thr Ile Ser Ser Gly Gly Gly Gly Ser Gly Gly Gly Gly Ser Gly Gly
        115                 120                 125

Gly Gly Ser Glu Leu Val Met Thr Gln Thr Pro Ser Ser Thr Ser Gly
    130                 135                 140

Ala Val Gly Gly Thr Val Thr Ile Asn Cys Gln Ala Ser Gln Ser Ile
145                 150                 155                 160

Asp Ser Asn Leu Ala Trp Phe Gln Gln Lys Pro Gly Gln Pro Pro Thr
                165                 170                 175

Leu Leu Ile Tyr Arg Ala Ser Asn Leu Ala Ser Gly Val Pro Ser Arg
            180                 185                 190

Phe Ser Gly Ser Arg Ser Gly Thr Glu Tyr Thr Leu Thr Ile Ser Gly
        195                 200                 205
```

```
Val Gln Arg Glu Asp Ala Ala Thr Tyr Tyr Cys Leu Gly Gly Val Gly
    210                 215                 220

Asn Val Ser Tyr Arg Thr Ser Phe Gly Gly Gly Thr Glu Val Val Val
225                 230                 235                 240

Lys

<210> SEQ ID NO 18
<211> LENGTH: 248
<212> TYPE: PRT
<213> ORGANISM: Artificial Sequence
<220> FEATURE:
<223> OTHER INFORMATION: scFV of the non-humanized R12 antibody

<400> SEQUENCE: 18

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Gly Gly Gly Ser Gly Gly
        115                 120                 125

Gly Gly Ser Gly Gly Gly Ser Glu Leu Val Leu Thr Gln Ser Pro
    130                 135                 140

Ser Val Ser Ala Ala Leu Gly Ser Pro Ala Lys Ile Thr Cys Thr Leu
145                 150                 155                 160

Ser Ser Ala His Lys Thr Asp Thr Ile Asp Trp Tyr Gln Gln Leu Gln
                165                 170                 175

Gly Glu Ala Pro Arg Tyr Leu Met Gln Val Gln Ser Asp Gly Ser Tyr
            180                 185                 190

Thr Lys Arg Pro Gly Val Pro Asp Arg Phe Ser Gly Ser Ser Ser Gly
        195                 200                 205

Ala Asp Arg Tyr Leu Ile Ile Pro Ser Val Gln Ala Asp Asp Glu Ala
    210                 215                 220

Asp Tyr Tyr Cys Gly Ala Asp Tyr Ile Gly Gly Tyr Val Phe Gly Gly
225                 230                 235                 240

Gly Thr Gln Leu Thr Val Thr Gly
                245

<210> SEQ ID NO 19
<211> LENGTH: 118
<212> TYPE: PRT
<213> ORGANISM: Artificial Sequence
<220> FEATURE:
<223> OTHER INFORMATION: VH of the non-humanized 2A2 antibody

<400> SEQUENCE: 19

Gln Val Gln Leu Gln Gln Ser Gly Ala Glu Leu Val Arg Pro Gly Ala
1               5                   10                  15
```

```
Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
            85                  90                  95

Thr Gly Tyr Tyr Asp Tyr Asp Ser Phe Thr Tyr Trp Gly Gln Gly Thr
            100                 105                 110

Leu Val Thr Val Ser Ala
            115

<210> SEQ ID NO 20
<211> LENGTH: 107
<212> TYPE: PRT
<213> ORGANISM: Artificial Sequence
<220> FEATURE:
<223> OTHER INFORMATION: VL of the non-humanized 2A2 antibody

<400> SEQUENCE: 20

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
            85                  90                  95

Thr Phe Gly Gly Gly Thr Lys Leu Glu Ile Lys
            100                 105

<210> SEQ ID NO 21
<211> LENGTH: 116
<212> TYPE: PRT
<213> ORGANISM: Artificial Sequence
<220> FEATURE:
<223> OTHER INFORMATION: VH of the non-humanized R11 antibody

<400> SEQUENCE: 21

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65                  70                  75                  80

Ser Leu Thr Thr Asp Asp Thr Ala Thr Tyr Phe Cys Ala Arg Gly Tyr
            85                  90                  95
```

Ser Thr Tyr Tyr Gly Asp Phe Asn Ile Trp Gly Pro Gly Thr Leu Val
            100                 105                 110

Thr Ile Ser Ser
        115

<210> SEQ ID NO 22
<211> LENGTH: 110
<212> TYPE: PRT
<213> ORGANISM: Artificial Sequence
<220> FEATURE:
<223> OTHER INFORMATION: VL of the non-humanized R11 antibody

<400> SEQUENCE: 22

Glu Leu Val Met Thr Gln Thr Pro Ser Ser Thr Ser Gly Ala Val Gly
1               5                   10                  15

Gly Thr Val Thr Ile Asn Cys Gln Ala Ser Gln Ser Ile Asp Ser Asn
            20                  25                  30

Leu Ala Trp Phe Gln Gln Lys Pro Gly Gln Pro Pro Thr Leu Leu Ile
        35                  40                  45

Tyr Arg Ala Ser Asn Leu Ala Ser Gly Val Pro Ser Arg Phe Ser Gly
    50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Val Gly Asn Val Ser
                85                  90                  95

Tyr Arg Thr Ser Phe Gly Gly Gly Thr Glu Val Val Val Lys
            100                 105                 110

<210> SEQ ID NO 23
<211> LENGTH: 121
<212> TYPE: PRT
<213> ORGANISM: Artificial Sequence
<220> FEATURE:
<223> OTHER INFORMATION: VH of the non-humanized R12 antibody

<400> SEQUENCE: 23

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120

<210> SEQ ID NO 24
<211> LENGTH: 112
<212> TYPE: PRT
<213> ORGANISM: Artificial Sequence
<220> FEATURE:
<223> OTHER INFORMATION: VL of the non-humanized R12 antibody -continued

<400> SEQUENCE: 24

```
Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Gly
                100                 105                 110
```

ROR1-SPECIFIC CHIMERIC ANTIGEN RECEPTORS (CAR) WITH HUMANIZED TARGETING DOMAINS

CROSS-REFERENCE TO RELATED APPLICATIONS

This application is a § 371 national phase of International Application No. PCT/EP2018/060887, filed on Apr. 27, 2018, which claims the benefit of European Application No. 17168805.4, filed on Apr. 28, 2017, all of which applications are incorporated by reference herein.

FIELD OF THE INVENTION

The invention relates to chimeric antigen receptors (CAR) with a humanized targeting domain specific to the antigen ROR1. The invention encompasses the polynucleotides, vectors encoding said CARs and the isolated cells expressing them at their surface, in particularly for their use in immunotherapy.

BACKGROUND OF THE INVENTION

The adoptive transfer of genetically modified T cells that express a T cell receptor or a chimeric antigen receptor (CAR) specific for a tumor-associated antigen is emerging as an effective modality for cancer therapy [1-5]. CARs are synthetic receptors most often constructed by linking a single chain variable fragment (scFV) of a monoclonal antibody (mAb) specific for a tumor cell surface molecule to a transmembrane domain, one or more intracellular costimulatory signaling modules, and CD3ζ [6-8]. CAR-modified T-cells confer non-MHC restricted recognition of tumor cells, and durable responses have been reported in patients with B-cell malignancies after treatment with autologous T-cells modified with CARs specific for the B-cell lineage restricted CD19 molecule. The major toxicities in these patients were related to tumor lysis, cytokine release, and prolonged depletion of normal B-lymphocytes [1-3, 5, 9]. A challenge in the field is to identify and validate receptor constructs specific for molecules that are expressed on a greater number of malignancies including common epithelial tumors, and that are restricted in their expression to malignant and not normal cells.

We have been investigating the receptor tyrosine kinase-like orphan receptor 1 (ROR1) as a candidate for immunotherapy with CAR-modified T-cells. ROR1 is a 120-kDa glycoprotein containing extracellular immunoglobulin (Ig)-like, Frizzled, and Kringle domains. ROR1 is expressed during embryogenesis but absent from normal adult tissues, apart from a subset of immature B-cell precursors, and low-level expression on adipocytes [10, 11]. ROR1 was first shown to be expressed in B-cell chronic lymphocytic leukemia (B-CLL) by transcriptional profiling [12, 13], and was subsequently identified on the surface of many cancers including mantle cell lymphoma (MCL), acute lymphoblastic leukemia (ALL) with a t(1;19) chromosome translocation, and a subset of lung, breast, colon, pancreas, renal, and ovarian cancers [14-21]. In both lung adenocarcinoma and t(1;19) ALL, ROR1 cooperates in oncogenic signaling, and knockdown of ROR1 with siRNA exposed a critical role for this molecule in maintaining tumor cell survival [15, 18, 22, 23]. WO 2016/115559 relates to antibodies and chimeric antigen receptors specific for ROR1.

Clinical trials with CD19 CARs have demonstrated that a paramount requirement for therapeutic effficacy is engraftment, in vivo proliferation and persistence of CAR T cells after adoptive transfer [24-26] (Clinical trial IDs: NCT02167360, NCT02030847 NCT01865617). In responding patients, CAR T cells undergo substantial proliferation, to a point where they comprise a substantial proportion of the patient's T-cell repertoire. Non-responding patients by contrast have an insufficient CAR T cell engraftment or the CAR T cell graft is rejected early after adoptive transfer. CAR T cell proliferation is an 'advanced' effector function, requiring optimal binding of the CAR targeting domain to the respective antigen. Therefore, to maximize the potential of CAR T cell therapy it is important to chose a CAR that exhibits strong antigen binding properties and also mediates high CAR T cell expansion and long-term survival.

All CARs that are currently used in the clinic contain scFv targeting domains that are derived from murine antibodies and the majoritiy of CARs that are in preclinical development also use targeting domains of 'foreign' origin. It has been noted that these 'foreign' targeting domains contain immunogenic epitopes that are recognized by the patient's immune system and elicit cellular or humoral immune responses that eventually mediate CAR-T cell rejection; see [27], [28] and [29]. Reference [30] describes the use of targeting domains from human antibodies.

In summary, there is a need in the art for improved CAR T cell constructs and related products and methods that can be used for therapies such as immunotherapies.

DESCRIPTION OF THE INVENTION

The present invention relates to humanized binding domains based on the known anti-ROR1 antibodies R11, R12 and 2A2 and to uses thereof for the construction of CARs and CAR engineered T cells. See, for instance, reference [14] for a description of the 2A2 antibody, which is hereby incorporated by reference in its entirety for all purposes; and reference [37] for a description of the R11/R12 antibodies, which is hereby incorporated by reference in its entirety for all purposes. The CARs according to the present invention have a higher degree of "human-ness" of the humanized R11, R12 and 2A2 binding domains, as opposed to the rabbit (R11 & R12) and mouse (2A2) binding domains. According to the invention, these CARs and CAR engineered T cells are expected to exhibit lower immunogenicity in clinical use in patients, as opposed to the rabbit (R11 & R12) and mouse (2A2) binding domains.

According to the invention, humanization can be carried out by any method that is known in the art. As a non-limiting example, humanization of the VH and VL domains of R11, R12 and 2A2 anti-ROR1 monoclonal antibodies has been performed by CDR grafting and selection of best binders for the ROR-1 target by Transpo-mAb Display. This method has been described for the R11 and 2A2 antibodies in reference [31], which is hereby incorporated by reference in its entirety for all purposes. According to the invention, recombinant mammalian cells expressing CARs such as CAR T cells can be produced to express CARs with the humanized anti-ROR1 binding domains of monoclonal anti-ROR-1 antibodies R11, R12 and 2A2.

Humanization of ROR1-specific CARs is different from the known clinical approaches which rely on non-humanized ROR1-specific CARs. The present inventors have now surprisingly shown that humanized ROR1-specific CARs have higher functionality than their non-humanized counterparts. This advantage was unexpected, because humanization is thought to decrease rather than increase affinity.

Furthermore, the inventors have surprisingly shown that humanized CARs with advantageous functional properties can be produced according to the invention. For instance, CAR T cells according to the invention are capable of target cell lysis and exhibit strong proliferation upon stimulation with lethally irradiated ROR1-expressing target cells.

Accordingly, the present invention provides the following preferred embodiments:

1. A ROR1-specific CAR comprising:
   a humanized targeting domain obtainable by humanization of a ROR1-binding fragment of a monoclonal antibody capable of binding to ROR1, wherein said monoclonal antibody is selected from the group consisting of the monoclonal antibodies R11, R12 and 2A2.
2. The ROR1-specific CAR according to item 1, wherein said monoclonal antibody is selected from the group consisting of the monoclonal antibodies R12 and 2A2.
3. A ROR1-specific CAR comprising a humanized targeting domain capable of binding to ROR1, wherein the humanized targeting domain comprises, preferably in an N- to C-terminal order:
   a) an antibody heavy chain variable domain amino acid sequence selected from the group consisting of:
      a1) the amino acid sequence of SEQ ID No: 1 or an amino acid sequence at least 90% identical thereto;
      a2) the amino acid sequence of SEQ ID No: 3 or an amino acid sequence at least 90% identical thereto; or
      a3) the amino acid sequence of SEQ ID No: 5 or an amino acid sequence at least 90% identical thereto;
   and
   b) an antibody light chain variable domain amino acid sequence selected from the group consisting of:
      b1) the amino acid sequence of SEQ ID No: 2 or an amino acid sequence at least 90% identical thereto;
      b2) the amino acid sequence of SEQ ID No: 4 or an amino acid sequence at least 90% identical thereto; or
      b3) the amino acid sequence of SEQ ID No: 6 or an amino acid sequence at least 90% identical thereto.
4. The ROR1-specific CAR according to item 3, wherein the humanized targeting domain comprises the antibody heavy chain variable domain amino acid sequence of SEQ ID No: 1 or an amino acid sequence at least 90% identical thereto and the antibody light chain variable domain amino acid sequence of SEQ ID No: 2 or an amino acid sequence at least 90% identical thereto.
5. The ROR1-specific CAR according to item 4, wherein the humanized targeting domain comprises the antibody heavy chain variable domain amino acid sequence of SEQ ID No: 1 and the antibody light chain variable domain amino acid sequence of SEQ ID No: 2.
6. The ROR1-specific CAR according to item 5, wherein the humanized targeting domain consists of the following sequences in an N- to C-terminal order: the antibody heavy chain variable domain amino acid sequence of SEQ ID No: 1, an amino acid linker sequence which is preferably the amino acid sequence of SEQ ID No: 8, and the antibody light chain variable domain amino acid sequence of SEQ ID No: 2.
7. The ROR1-specific CAR according to item 3, wherein the humanized targeting domain comprises the antibody heavy chain variable domain amino acid sequence of SEQ ID No: 3 or an amino acid sequence at least 90% identical thereto and the antibody light chain variable domain amino acid sequence of SEQ ID No: 4 or an amino acid sequence at least 90% identical thereto.
8. The ROR1-specific CAR according to item 7, wherein the humanized targeting domain comprises the antibody heavy chain variable domain amino acid sequence of SEQ ID No: 3 and the antibody light chain variable domain amino acid sequence of SEQ ID No: 4.
9. The ROR1-specific CAR according to item 8, wherein the humanized targeting domain consists of the following sequences in an N- to C-terminal order: the antibody heavy chain variable domain amino acid sequence of SEQ ID No: 3, an amino acid linker sequence which is preferably the amino acid sequence of SEQ ID No: 8, and the antibody light chain variable domain amino acid sequence of SEQ ID No: 4.
10. The ROR1-specific CAR according to item 3, wherein the humanized targeting domain comprises the antibody heavy chain variable domain amino acid sequence of SEQ ID No: 5 or an amino acid sequence at least 90% identical thereto and the antibody light chain variable domain amino acid sequence of SEQ ID No: 6 or an amino acid sequence at least 90% identical thereto.
11. The ROR1-specific CAR according to item 10, wherein the humanized targeting domain comprises the antibody heavy chain variable domain amino acid sequence of SEQ ID No: 5 and the antibody light chain variable domain amino acid sequence of SEQ ID No: 6.
12. The ROR1-specific CAR according to item 11, wherein the humanized targeting domain consists of the following sequences in an N- to C-terminal order: the antibody heavy chain variable domain amino acid sequence of SEQ ID No: 5, an amino acid linker sequence which is preferably the amino acid sequence of SEQ ID No: 8, and the antibody light chain variable domain amino acid sequence of SEQ ID No: 6.
13. A combination of CARs comprising at least a first and a second CAR, the combination being ROR1-specific, wherein said first and said second CAR are present on different polypeptide chains, and wherein:
   c) said first CAR comprises a first humanized targeting domain comprising an antibody heavy chain variable domain amino acid sequence selected from the group consisting of:
      c1) the amino acid sequence of SEQ ID No: 1 or an amino acid sequence at least 90% identical thereto;
      c2) the amino acid sequence of SEQ ID No: 3 or an amino acid sequence at least 90% identical thereto; or
      c3) the amino acid sequence of SEQ ID No: 5 or an amino acid sequence at least 90% identical thereto;
   and
   d) said second CAR comprises a second humanized targeting domain comprising an antibody light chain variable domain amino acid sequence selected from the group consisting of:
      d1) the amino acid sequence of SEQ ID No: 2 or an amino acid sequence at least 90% identical thereto;
      d2) the amino acid sequence of SEQ ID No: 4 or an amino acid sequence at least 90% identical thereto; or
      d3) the amino acid sequence of SEQ ID No: 6 or an amino acid sequence at least 90% identical thereto.
14. The combination according to item 13, wherein the first humanized targeting domain comprises the antibody heavy chain variable domain amino acid sequence of SEQ ID No: 1 or an amino acid sequence at least 90% identical thereto and the second humanized targeting domain comprises the antibody light chain variable domain amino acid sequence of SEQ ID No: 2 or an amino acid sequence at least 90% identical thereto.
15. The combination according to item 14, wherein the first humanized targeting domain comprises the antibody heavy chain variable domain amino acid sequence of SEQ ID No: 1 and the second humanized targeting domain comprises the antibody light chain variable domain amino acid sequence of SEQ ID No: 2.
16. The combination according to item 13, wherein the first humanized targeting domain comprises the antibody heavy chain variable domain amino acid sequence of SEQ ID No: 3 or an amino acid sequence at least 90% identical thereto and the second humanized targeting domain comprises the antibody light chain variable domain amino acid sequence of SEQ ID No: 4 or an amino acid sequence at least 90% identical thereto.
17. The combination according to item 16, wherein the first humanized targeting domain comprises the antibody heavy chain variable domain amino acid sequence of SEQ ID No: 3 and the second humanized targeting domain comprises the antibody light chain variable domain amino acid sequence of SEQ ID No: 4.
18. The combination according to item 13, wherein the first humanized targeting domain comprises the antibody heavy chain variable domain amino acid sequence of SEQ ID No: 5 or an amino acid sequence at least 90% identical thereto and the second humanized targeting domain comprises the antibody light chain variable domain amino acid sequence of SEQ ID No: 6 or an amino acid sequence at least 90% identical thereto.
19. The combination according to item 18, wherein the first humanized targeting domain comprises the antibody heavy chain variable domain amino acid sequence of SEQ ID No: 5 and the second humanized targeting domain comprises the antibody light chain variable domain amino acid sequence of SEQ ID No: 6.
20. The ROR1-specific CAR according to any one of the preceding items, wherein the CAR further comprises a costimulatory domain capable of mediating costimulation to immune cells; or the combination according to any one of the preceding items, wherein at least the first or the second CAR of the combination, preferably at least the first and the second CAR of the combination, most preferably all of the CARs of the combination, further comprise a costimulatory domain capable of mediating costimulation to immune cells.
21. The ROR1-specific CAR or the combination according to item 20, wherein said costimulatory domain is from 4-1BB, CD28, Ox40, ICOS or DAP10.
22. The ROR1-specific CAR or the combination according to item 21, wherein said costimulatory domain has the amino acid sequence of SEQ ID No: 12.
23. The ROR1-specific CAR according to any one of the preceding items, further comprising a transmembrane polypeptide; or the combination according to any one of the preceding items, wherein at least the first or the second CAR of the combination, preferably at least the first and the second CAR of the combination, most preferably all of the CARs of the combination, further comprise a transmembrane polypeptide.
24. The ROR1-specific CAR or the combination according to item 23, wherein said transmembrane polypeptide is a transmembrane domain from CD4, CD8 or CD28.
25. The ROR1-specific CAR or the combination according to item 24, wherein said transmembrane domain has the amino acid sequence of SEQ ID No: 11.
26. The ROR1-specific CAR according to any one of the preceding items, further comprising a CAR spacer domain; or the combination according to any one of the preceding items, wherein at least the first or the second CAR of the combination, preferably at least the first and the second CAR of the combination, most preferably all of the CARs of the combination, further comprise a CAR spacer domain.
27. The ROR1-specific CAR or the combination according to item 26, wherein said CAR spacer domain is from CD4, CD8, an FC-receptor, an immunoglobulin, or an antibody.
28. The ROR1-specific CAR or the combination according to item 27, wherein said CAR spacer domain has the amino acid sequence of SEQ ID No: 9 or SEQ ID No: 10, preferably the amino acid sequence of SEQ ID No: 9.
29. The ROR1-specific CAR according to any one of the preceding items, further comprising a suicide gene product that allows the selective killing of CAR T cells; or the combination according to any one of the preceding items, wherein at least the first or the second CAR of the combination further comprises a suicide gene product that allows the selective killing of CAR T cells.
30. The ROR1-specific CAR or the combination according to item 29, wherein said suicide gene product is iCasp9 or HSV-TK.
31. The ROR1-specific CAR according to any one of the preceding items, comprising, in an N- to C-terminal order: i) a signal peptide for direction into the endoplasmic reticulum, the signal peptide preferably having the amino acid sequence of SEQ ID No: 7; ii) said humanized targeting domain; iii) the CAR spacer domain according to any one of items 26 to 28; iv) the transmembrane polypeptide according to any one of items 23-25; v) the costimulatory domain according to any one of items 20-22; vi) a CD3z signaling domain preferably having the amino acid sequence of SEQ ID No: 13; and optionally further comprising: vii) a T2A ribosomal skipping sequence preferably having the amino acid sequence of SEQ ID No: 14; viii) a signal peptide for direction into the endoplasmic reticulum, the signal peptide preferably having the amino acid sequence of SEQ ID No: 7; and ix) a detectable marker protein sequence preferably having the EGFRt amino acid sequence of SEQ ID No: 15.
32. The ROR1-specific CAR according to item 31, consisting of said components i) to ix).
33. A polynucleotide encoding the ROR1-specific CAR according to any one of the preceding items.
34. A recombinant mammalian cell expressing at least one ROR1-specific CAR according to any one of the preceding items or expressing the combination of CARs according to any one of the preceding items.
35. The recombinant mammalian cell according to item 34, wherein said cell is an immune cell.
36. The recombinant mammalian cell according to any one of the preceding items, wherein said cell is a lymphocyte.
37. The recombinant mammalian cell according to any one of the preceding items, wherein said lymphocyte is a B lymphocyte or T lymphocyte.
38. The recombinant mammalian cell according to item 34, wherein said cell is a $CD8^+$ killer T cell, a $CD4^+$ helper T cell, a naive T cell, a memory T cell, a central memory T cell, an effector memory T cell, a memory stem T cell, an invariant T cell, an NKT cell, a cytokine induced killer T cell, a g/d T cell, a natural killer cell, a monocyte, a macrophage, a dendritic cell, or a granulocyte.
39. The recombinant mammalian cell according to any one of the preceding items, wherein the cell is a human cell.

40. The recombinant mammalian cell according to any one of the preceding items, wherein the recombinant mammalian cell is capable of at least one cell division when cocultured with lethally irradiated ROR1-expressing target cells at an E:T ratio of 4:1 for 72 h in the absence of exogenous cytokines.
41. The recombinant mammalian cell according to any one of the preceding items, wherein the recombinant mammalian cell is capable of at least two cell divisions when cocultured with lethally irradiated ROR1-expressing target cells at an E:T ratio of 4:1 for 72 h in the absence of exogenous cytokines.
42. The recombinant mammalian cell according to any one of the preceding items, wherein the recombinant mammalian cell is capable of at least three cell divisions when cocultured with lethally irradiated ROR1-expressing target cells at an E:T ratio of 4:1 for 72 h in the absence of exogenous cytokines.
43. The recombinant mammalian cell according to any one of the preceding items, wherein the recombinant mammalian cell is capable of at least four cell divisions when cocultured with lethally irradiated ROR1-expressing target cells at an E:T ratio of 4:1 for 72 h in the absence of exogenous cytokines.
44. The recombinant mammalian cell according to any one of the preceding items, wherein the recombinant mammalian cell is capable of at least five cell divisions when cocultured with lethally irradiated ROR1-expressing target cells at an E:T ratio of 4:1 for 72 h in the absence of exogenous cytokines.
45. The recombinant mammalian cell according to any one of the preceding items, wherein the ROR1-specific CAR or the ROR1-specific combination of CARs is capable of binding to ROR1 with higher binding affinity than a respective recombinant mammalian control cell expressing a respective ROR1-specific CAR or a respective ROR1-specific combination of CARs where none of the targeting domains is humanized, and wherein said binding affinity is binding affinity to fluorescently labelled recombinant aggregated ROR1 as assessed by flow cytometry analysis.
46. A method for producing a recombinant mammalian cell according to any one of the preceding items, the method comprising the steps of:
  (a) providing a mammalian cell;
  (b) introducing into said mammalian cell of step (a) at least one polynucleotide encoding said at least one ROR1-specific CAR or said combination of CARs; and
  (c) expressing said at least one ROR1-specific CAR or said combination of CARs from said at least one polynucleotide in said cell;
  thereby obtaining said recombinant mammalian cell.
47. The method of item 46, further comprising coculturing the recombinant mammalian cell with lethally irradiated ROR1-expressing target cells at a ratio of 4:1 for 72 h in the absence of exogenous cytokines.
48. The method of item 47, wherein at least 1%, preferably at least 2%, more preferably at least 3%, and still more preferably at least 4% of the recombinant mammalian cells undergo at least 5 cell divisions during the coculturing.
49. The method according to any one of the preceding items, wherein said method is an in vitro method.
50. The method according to any one of the preceding items, wherein said mammalian cells of step (a) are cells obtained from donors.
51. The method according to any one of the preceding items, wherein said mammalian cells of step (a) are cells obtained from patients.
52. A recombinant mammalian cell according to any one of the preceding items for use in medicine.
53. A recombinant mammalian cell according to any one of the preceding items for use in a method for treating a cancer that expresses ROR1 in a patient.
54. The recombinant mammalian cell according to item 53 for the use according to item 53, wherein the cancer is ROR1-positive leukemia, mantle cell lymphoma, breast-cancer or lung cancer.
55. A method for treating a patient in need thereof, the method comprising administering a recombinant mammalian cell according to any one of the preceding items to said patient.
56. The method according to item 55, wherein the method is for treating a cancer that expresses ROR1.
57. The method according to item 56, wherein the cancer is ROR1-positive leukemia, mantle cell lymphoma, breast-cancer or lung cancer.

BRIEF DESCRIPTION OF THE DRAWINGS

FIG. 1: Amino acid sequences of the humanized 2A2 VH and VL sequences and the complete h2A2 CAR coding sequence
  (A) Humanized 2A2 VH and VL amino acid sequences
  (B) Complete amino acid sequence of the h2A2 CAR, represented in an N- to C-terminal order. Note that the asterisk denotes the end of the amino acid sequence.
FIG. 2: Amino acid sequences of the humanized R11 VH and VL sequences and the complete R11 CAR coding sequence
  (A) Humanized R11 VH and VL amino acid sequences
  (B) Complete amino acid sequence of the R11 CAR, represented in an N- to C-terminal order. Note that the asterisk denotes the end of the amino acid sequence.
FIG. 3: Amino acid sequences of the humanized R12 VH and VL sequences and the complete R12 CAR coding sequence
  (A) Humanized R12 VH and VL amino acid sequences
  (B) Complete amino acid sequence of the R12 CAR, represented in an N- to C-terminal order. Note that the asterisk denotes the end of the amino acid sequence.

DETAILED DESCRIPTION OF THE INVENTION

Figure 4B:
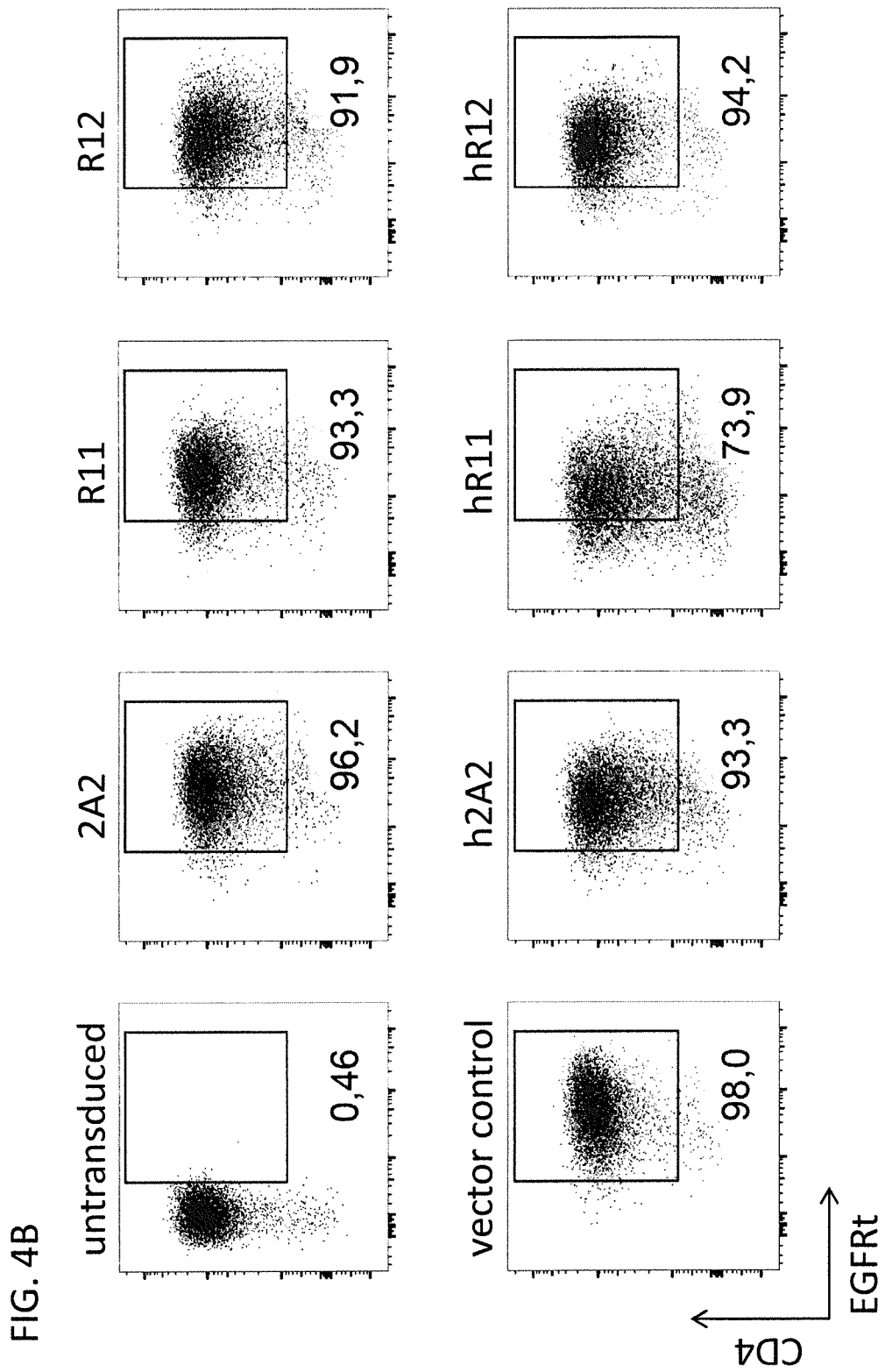
FIG. 4: Enrichment and detection of CAR by EGFRt transduction marker
Human CD4 or CD8 positive T cells were transduced with lentiviral vector encoding a humanized or non-humanized ROR1 CAR and subsequently enriched for CAR expressing cells by magnetic activated cell sorting (MACS) making use of the truncated epidermal growth factor receptor (EGFRt) transduction marker. The coding sequence (CDS) for EGFRt is linked to the CAR CDS by a 2A ribosomal skipping sequence and expression of EGFRt can be used as a surrogate marker for CAR expression.
  (A) Flow cytometry plots demonstrating the frequency of EGFRt-positive $CD4^+$ T cells after EGFRt enrichment by MACS.
  (B) Flow cytometry plots demonstrating the frequency of EGFRt-positive $CD8^+$ T cells after EGFRt enrichment by MACS.

Unless specifically defined herein, all technical and scientific terms used herein have the same meaning as commonly understood by a skilled artisan in the fields of gene therapy, immunology, biochemistry, genetics, and molecular biology.

All methods and materials similar or equivalent to those described herein can be used in the practice or testing of the present invention, with suitable methods and materials being described herein. All publications, patents and patent applications cited herein are hereby incorporated by reference in their entirety for all purposes. References referred to herein are indicated by a reference number in square brackets (e.g. as "[31]" or as "reference [31]"), which refers to the respective reference in the list of references at the end of the description. In case of conflict, the present specification, including definitions, will prevail over the cited references. Further, the materials, methods, and examples are illustrative only and are not intended to be limiting, unless otherwise specified.

Antibodies of non-human origin can be humanized by CDR grafting by methods known in the art. The humanization increases the homology of the binding domains to human antibody binding domains (i.e. the humanness), and reduces the immunogenic potential of the humanized antibody in human beings, which in turn is expected to increase the safety and therapeutic application profile in human patients. On the other hand, antibody humanization is often accompanied by a reduction of the binding affinity of the humanized antibody to its antigen, often requiring tedious affinity maturation, see reference [32], which is hereby incorporated by reference in its entirety for all purposes. It has also been experienced that the use of humanized antibody fragments for the generation of a targeting domain of a CAR can result in a lower performance of the CAR in respect to binding to the target antigen and triggering effector functions of the CAR expressing cell.

In the present invention the inventors have fused humanized VH and VL domains, as exemplified in FIGS. 1-3, of antibodies originating from the anti-ROR1-specific antibody clones 2A2 (*Mus musculus*, WO2010/124188, which is hereby incorporated by reference in its entirety for all purposes), R11 and R12 (*Oryctolagus cuniculus*, WO2012/075158, which is hereby incorporated by reference in its entirety for all purposes). The humanized VH and VL domains of these antibodies were then used to design single chain variable fragments (scFvs) that were further used for the design of CARs targeting the ROR1 antigen. Gene transfer vectors were created that allow the transduction or transfection of primary human T cells with the humanized CARs and allow the production of a CAR T cell product. The effector functions of the CAR T cells expressing ROR1 CARs with humanized ROR1 targeting domains were compared to their non-humanized counterparts. The humanized ROR1 CARs h2A2 and hR12 have conferred unexpected superior effector functions compared to their non-humanized counterparts.

The present invention describes for the first time the generation of humanized ROR1 CARs and their usage to redirect immune cells for the killing of ROR1 expressing target cells. Unexpectedly, the observed activity of two of the humanized CARs, namely h2A2 and hR12, was higher than the non-humanized forms in functional T cells assays with ROR1-expressing target cells. In contrast, the CAR that was constructed with an scFv targeting domain that originated from the R11 monoclonal antibody showed a comparatively strong reduction of effector functions, thus demonstrating the commonly expectable decline in therapeutic potential.

The finding of the present invention, that humanized ROR1 CARs can mediate antigen-specific effector functions to immune cells that are superior to those of the non-humanized counterparts is unexpected and has, to the inventors' knowledge, not been disclosed in the prior art. This finding is also unexpected, because antibody humanization is often accompanied by a loss of affinity, and/or a reduction of affinity to the target antigen. CARs whose targeting domain originates from such humanized antibodies oftentimes also exhibit lower effector functions and less therapeutic potential. It could thus neither be anticipated nor expected that our humanized ROR1 CARs demonstrate effector functions that are superior to their non-humanized counterparts.

The significantly higher function in combination with the anticipated lower immunogenicity of our novel humanized ROR1 CARs provides a substantial advantage for the clinical application of these CARs, especially, but not limited to, their usage in the context of immunotherapy against cancer.

A "recombinant mammalian cell" according to the invention can be any cell as defined herein. Preferably, a recombinant mammalian cell is an isolated cell. Recombinant mammalian cells according to the invention can be produced in accordance with known pharmaceutical standards. For instance, they can be formulated for administration to humans.

A ROR1-specific CAR or a combination of CARs according to the invention can be any possible form. In a preferred embodiment, the ROR1-specific CAR or combination of CARs is present in an isolated form. In another preferred embodiment the ROR1-specific CAR or combination of CARs according to the invention can be present in a composition, The composition may be a pharmaceutical composition.

Sequence alignments of sequences according to the invention are performed by suitable algorithms, and preferably by using the BLAST algorithm, see references [33, 34], using suitable alignment parameters as known in the art.

As used herein, each occurrence of terms such as "comprising" or "comprises" may optionally be substituted with "consisting of" or "consists of".

The sequences corresponding to the SEQ IDs referred to herein are indicated in FIGS. 1 to 3 and in the following tables:

GMCSF signal peptide
(SEQ ID No: 7)
MLLLVTSLLLCELPHPAFLLIP h2A2 heavy chain variable domain (VH)
(SEQ ID No: 1)
EVQLVQSGAEVKKPGASVKVSCKASGYTFSDYEMHWVRQAPGQGLEWLGA

IDPETGGTAYNQKFKGRVTMTGDTSISTAYMELSRLTSDDTAVYYCTGYY

DYDSFTYWGQGTLVSVSS

4(GS)x3 linker
(SEQ ID No: 8)
GGGGSGGGGSGGGGS h2A2 light chain variable domain (VL)
(SEQ ID No: 2)
DIQMTQSPSSLSTSVGDRVTITCKASQNVDAAVAWYQQKPGKAPKLLIYS

ASNRYTGVASRFSGSGSGTDFTFTISSLQSEDLADYFCQQYDIYPYTFGQ

GTKLEIK

IgG4 hinge domain
(SEQ ID No: 9)
ESKYGPPCPPCP

CD28 transmembrane domain
(SEQ ID No: 11)
MFWVLVVVGGVLACYSLLVTVAFIIFWV 4-1BB costimulatory domain
(SEQ ID No: 12)
KRGRKKLLYIFKQPFMRPVQTTQEEDGCSCRFPEEEEGGCEL CD3z signaling domain
(SEQ ID No: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

T2A ribosomal skipping sequence
(SEQ ID No: 14)
LEGGGEGRGSLLTCGDVEENPGPR

GMCSF signal peptide
(SEQ ID No: 7)
MLLLVTSLLLCELPHPAFLLIP

EGFRt
(SEQ ID No: 15)
RKVCNGIGIGEFKDSLSINATNIKHFKNCTSISGDLHILPVAFRGDSFTH

TPPLDPQELDILKTVKEITGFLLIQAWPENRTDLHAFENLEIIRGRTKQH

GQFSLAVVSLNITSLGLRSLKEISDGDVIISGNKNLCYANTINWKKLFGT

SGQKTKIISNRGENSCKATGQVCHALCSPEGCWGPEPRDCVSCRNVSRGR

ECVDKCNLLEGEPREFVENSECIQCHPECLPQAMNITCTGRGPDNCIQCA

HYIDGPHCVKTCPAGVMGENNTLVWKYADAGHVCHLCHPNCTYGCTGPGL

EGCPTNGPKIPSIATGMVGALLLLLVVALGIGLFM

GMCSF signal peptide
(SEQ ID No: 7)
MLLLVTSLLLCELPHPAFLLIP hR11 heavy chain variable domain (VH)
(SEQ ID No: 3)
EVQLVQSGGGLVQPGGSLRLSCAASGSDINDYPISWVRQAPGKGLEWVSF

INSGGSTWYASWVKGRFTISRDNAKNSLYLQMNSLRDDDTATYFCARGYS

TYYGDFNIWGQGTLVTVSS

4(GS)x3 linker
(SEQ ID No: 8)
GGGGSGGGGSGGGGS hR11 light chain variable domain (VL)
(SEQ ID No: 4)
DIVMTQSPSSLSASVGDRVTITCQASQSIDSNLAWFQQKPGKAPKSLIYR

ASNLASGVPSKFSGSGSGTDFTLTISSLQREDAATYYCLGGVGNVSYRTS

FGGGTKVEIK

IgG4 CH2CH3 4/2NQ
(SEQ ID No: 10)
ESKYGPPCPPCPAPPVAGPSVFLFPPKPKDTLMISRTPEVTCVVVDVSQE
DPEVQFNWYVDGVEVHNAKTKPREEQFQSTYRVVSVLTVLHQDWLNGKEY
KCKVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSRWQE
GNVFSCSVMHEALHNHYTQKSLSLSLGK

CD28 transmembrane domain
(SEQ ID No: 11)
MFWVLVVVGGVLACYSLLVTVAFIIFWV 4-1BB costimulatory domain
(SEQ ID No: 12)
KRGRKKLLYIFKQPFMRPVQTTQEEDGCSCRFPEEEEGGCEL CD3z signaling domain
(SEQ ID No: 13)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR T2A ribosomal skipping sequence
(SEQ ID No: 14)
LEGGGEGRGSLLTCGDVEENPGPR GMCSF signal peptide
(SEQ ID No: 7)
MLLLVTSLLLCELPHPAFLLIP EGRFt
(SEQ ID No: 15)
RKVCNGIGIGEFKDSLSINATNIKHFKNCTSISGDLHILPVAFRGDSFTH
TPPLDPQELDILKTVKEITGFLLIQAWPENRTDLHAFENLEIIRGRTKQH
GQFSLAVVSLNITSLGLRSLKEISDGDVIISGNKNLCYANTINWKKLFGT
SGQKTKIISNRGENSCKATGQVCHALCSPEGCWGPEPRDCVSCRNVSRGR
ECVDKCNLLEGEPREFVENSECIQCHPECLPQAMNITCTGRGPDNCIQCA
HYIDGPHCVKTCPAGVMGENNTLVWKYADAGHVCHLCHPNCTYGCTGPGL
EGCPTNGPKIPSIATGMVGALLLLLVVALGIGLFM GMCSF signal peptide
(SEQ ID No: 7)
MLLLVTSLLLCELPHPAFLLIP hR12 heavy chain variable domain (VH)
(SEQ ID No: 5)
QVQLVESGGALVQPGGSLTLSCKASGFDFSAYYMSWVRQAPGKGLEWIAT
IYPSSGKTYYAASVQGRFTISADNAKNTVYLQMNSLTAADTATYFCARDS
YADDGALFNIWGQGTLVTVSS 4(GS)x3 linker
(SEQ ID No: 8)
GGGGSGGGGSGGGGS hR12 light chain variable domain (VL)
(SEQ ID No: 6)
QLVLTQSPSVSAALGSSAKITCTLSSAHKTDTIDWYQQLAGQAPRYLMYV
QSDGSYEKRSGVPDRFSGSSSGADRYLIISSVQADDEADYYCGADYIGGY
VFGGGTQLTVG IgG4 hinge domain
(SEQ ID No: 9)
ESKYGPPCPPCP CD28 transmembrane domain
(SEQ ID No: 11)
MFWVLVVVGGVLACYSLLVTVAFIIFWV 4-1BB costimulatory domain
(SEQ ID No: 12)
KRGRKKLLYIFKQPFMRPVQTTQEEDGCSCRFPEEEEGGCEL CD3z signaling domain
(SEQ ID No: 13)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR T2A ribosomal skipping sequence
(SEQ ID No: 14)
LEGGGEGRGSLLTCGDVEENPGPR GMCSF signal peptide
(SEQ ID No: 7)
MLLLVTSLLLCELPHPAFLLIP EGFRt
(SEQ ID No: 15)
RKVCNGIGIGEFKDSLSINATNIKHFKNCTSISGDLHILPVAFRGDSFTH
TPPLDPQELDILKTVKEITGFLLIQAWPENRTDLHAFENLEIIRGRTKQH
GQFSLAVVSLNITSLGLRSLKEISDGDVIISGNKNLCYANTINWKKLFGT
SGQKTKIISNRGENSCKATGQVCHALCSPEGCWGPEPRDCVSCRNVSRGR
ECVDKCNLLEGEPREFVENSECIQCHPECLPQAMNITCTGRGPDNCIQCA
HYIDGPHCVKTCPAGVMGENNTLVWKYADAGHVCHLCHPNCTYGCTGPGL
EGCPTNGPKIPSIATGMVGALLLLLVVALGIGLFM Additionally, preferred amino acid sequences of ROR1-binding fragments of the non-humanized monoclonal antibodies R11, R12 and 2A2 that can be used as starting sequences for humanization in accordance with the invention are as indicated below:

scFV of the non-humanized 2A2 antibody
(SEQ ID No: 16):
QVQLQQSGAELVRPGASVTLSCKASGYTFSDYEMHWVIQTPVHGLEWIGA
IDPETGGTAYNQKFKGKAILTADKSSSTAYMELRSLTSEDSAVYYCTGYY
DYDSFTYWGQGTLVTVSAGGGGSGGGGSGGGGSDIVMTQSQKIMSTTVGD
RVSITCKASQNVDAAVAWYQQKPGQSPKLLIYSASNRYTGVPDRFTGSGS
GTDFTLTISNMQSEDLADYFCQQYDIYPYTFGGGTKLEIK scFV of the non-humanized R11 antibody
(SEQ ID No: 17):
QSVKESEGDLVTPAGNLTLTCTASGSDINDYPISWVRQAPGKGLEWIGFI
NSGGSTWYASWVKGRFTISRTSTTVDLKMTSLTTDDTATYFCARGYSTYY
GDFNIWGPGTLVTISSGGGGSGGGGSGGGGSELVMTQTPSSTSGAVGGTV
TINCQASQSIDSNLAWFQQKPGQPPTLLIYRASNLASGVPSRFSGSRSGT
EYTLTISGVQREDAATYYCLGGVGNVSYRTSFGGGTEVVVK -continued scFV of the non-humanized R12 antibody
(SEQ ID No: 18):
QEQLVESGGRLVTPGGSLTLSCKASGFDFSAYYMSWVRQAPGKGLEWIAT

IYPSSGKTYYATWVNGRFTISSDNAQNTVDLQMNSLTAADRATYFCARDS

YADDGALFNIWGPGTLVTISSGGGGSGGGGSGGGGSELVLTQSPSVSAAL

GSPAKITCTLSSAHKTDTIDWYQQLQGEAPRYLMQVQSDGSYTKRPGVPD

RFSGSSSGADRYLIIPSVQADDEADYYCGADYIGGYVFGGGTQLTVTG

VH of the non-humanized 2A2 antibody
(SEQ ID No: 19):
QVQLQQSGAELVRPGASVTLSCKASGYTFSDYEMHWVIQTPVHGLEWIGA

IDPETGGTAYNQKFKGKAILTADKSSSTAYMELRSLTSEDSAVYYCTGYY

DYDSFTYWGQGTLVTVSA

VL of the non-humanized 2A2 antibody
(SEQ ID No: 20):
DIVMTQSQKIMSTTVGDRVSITCKASQNVDAAVAWYQQKPGQSPKLLIYS

ASNRYTGVPDRFTGSGSGTDFTLTISNMQSEDLADYFCQQYDIYPYTFGG

GTKLEIK

VH of the non-humanized R11 antibody
(SEQ ID No: 21):
QSVKESEGDLVTPAGNLTLTCTASGSDINDYPISWVRQAPGKGLEWIGFI

NSGGSTWYASWVKGRFTISRTSTTVDLKMTSLTTDDTATYFCARGYSTYY

GDFNIWGPGTLVTISS

VL of the non-humanized R11 antibody
(SEQ ID No: 22):
ELVMTQTPSSTSGAVGGTVTINCQASQSIDSNLAWFQQKPGQPPTLLIYR

ASNLASGVPSRFSGSRSGTEYTLTISGVQREDAATYYCLGGVGNVSYRTS

FGGGTEVVVK

VH of the non-humanized R12 antibody
(SEQ ID No: 23):
QEQLVESGGRLVTPGGSLTLSCKASGFDFSAYYMSWVRQAPGKGLEWIAT

IYPSSGKTYYATWVNGRFTISSDNAQNTVDLQMNSLTAADRATYFCARDS

YADDGALFNIWGPGTLVTISS

VL of the non-humanized R12 antibody
(SEQ ID No: 24):
ELVLTQSPSVSAALGSPAKITCTLSSAHKTDTIDWYQQLQGEAPRYLMQV

QSDGSYTKRPGVPDRFSGSSSGADRYLIIPSVQADDEADYYCGADYIGGY

VFGGGTQLTVTG

FURTHER PREFERRED EMBODIMENTS

A preferred embodiment of the humanized CARs of the invention is their application in cellular immunotherapy against malignancies that are associated with the aberrant occurrence of ROR1-expressing cells. Preferably, the CAR modified cell is a CD8+ killer T cell, a CD4+ helper T cell, a naïve T cell, a memory T cell, a central memory T cells, an effector memory T cell, a memory stem T cell, an invariant T cell, an NKT cell, a cytokine induced killer T cell, a gamma/delta T cell, a B lymphocyte, a natural killer cell, a monocyte, a macrophage, a dendritic cell, a granulocyte, or any other mammalian cell type desirable to be used for genetic modification.

A particularly preferred embodiment is the usage use of CARs of the invention with humanized targeting domains originating from the 2A2, R11 or R12 monoclonal antibody as immunotherapeutic agents against ROR1-positive leukemia, mantle cell lymphoma, breast-cancer, lung cancer or any other cancer that expresses ROR1.

Another preferred embodiment is the usage use of CARs of the invention with humanized targeting domains originating from the 2A2, R11 or R12 monoclonal antibody as immunotherapeutic agents for the treatment of obesity.

Another preferred embodiment is the usage use of CARs of the invention with humanized targeting domains originating from the 2A2, R11 or R12 monoclonal antibody as immunotherapeutic agents against ROR1-positive autoimmune or infectious diseases.

Another preferred embodiment is the use of the humanized targeting domains of the invention as component of CARs containing a single costimulatory domain, including but not limited to 4-1BB, CD28, Ox40, ICOS, DAP10 or any other domain that provides costimulation to immune cells.

In another embodiment the humanized targeting domains of the invention may be used as components of a CAR that mediates an inhibitory signal due to the usage of a co-inhibitory signaling domain. Such signaling domains can originate from the co-inhibitory receptors CTLA-4, PD-1, BTLA, LAG3, TIM3 or any other receptor that inhibits immune cell functions.

Another preferred embodiment is the usage of the humanized targeting domains of the invention in a CAR that encompasses a combination of two or more costimulatory or co-inhibitory domains.

In another embodiment, the humanized targeting domains of the invention may be used in a format that is different from the presented scFv format to be included into a CAR construct. As a non-limiting example such CARs may be composed of two different polypeptide chains from which one chain encompasses the variable heavy chain (VH) and one chain encompasses the variable light (VL) chain of the disclosed humanized anti-ROR1 antibodies.

In another preferred embodiment the CAR gene, containing a humanized targeting domain of the invention, is transferred into the desired cells by non-viral transfection methods like electroporation, nucleofection or together with a transposase like Sleeping Beauty, PiggyBac, Frog Prince, Himarl, Passport, Minos, hAT, Tol1, Tol2, AciDs, PIF, Harbinger, Harbinger3-DR, and Hsmar1, or any of their respective derivatives with equal, lower and/or higher transposition activity.

In another preferred embodiment the CAR gene encompassing a humanized targeting domain originating of the invention is delivered as a part of a RNA or DNA polynucleotide molecule.

EXAMPLES

The present invention is exemplified by the following non-limiting examples:

Example 1

Preparation and Functional Testing of ROR1-Specific CAR-Modified Human CD8+ and CD4+ T Cells with Humanized Targeting Domains Materials and Methods:
Human Subjects Blood samples were obtained from healthy donors who provided written informed consent to participate in research protocols approved by the Institutional Review Board of the University of Würzburg (Universitätsklinikum Würzburg, UKW). Peripheral blood mononuclear cells (PBMC) were isolated by centrifugation over Ficoll-Hypaque (Sigma, St. Louis, Mo.).

Cell Lines

The 293T, K562, MDA-MB-231 and A549 cell lines were obtained from the American Type Culture Collection. K562-ROR1 were generated by lentiviral transduction with the full-length ROR1-gene. Luciferase expressing lines were derived by lentiviral transduction of the above mentioned cell lines with the firefly (*P. pyralis*) luciferase (ffluc)-gene. The cells were cultured in Dulbecco's modified Eagle's medium supplemented with 10% fetal calf serum and 100 U/ml penicillin/streptomycin.

Immunophenotyping

PBMC and T cell lines were stained with one or more of the following conjugated mAb: CD3, CD4, CD8 and matched isotype controls (BD Biosciences, San Jose, Calif.). Transduced T cell lines were stained with biotin-conjugated anti-EGFR antibody (ImClone Systems Incorporated, Branchburg, N.J.) and streptavidin-PE (BD Biosciences, San Jose, Calif.). Staining with 7-AAD (BD Biosciences) was performed for live/dead cell discrimination as directed by the manufacturer. Flow analyses were done on a FACSCanto and data analyzed using FlowJo software (Treestar, Ashland, Oreg.).

Lentiviral Vector Construction, Preparation of Lentivirus, and Generation of CAR-T Cells The construction of epHIV7 lentiviral vectors containing ROR1-specific CARs with a short or long spacer and a 4-1BB costimulatory domain has been described, see reference [35], which is hereby incorporated by reference in its entirety for all purposes. All CAR constructs encoded a truncated epidermal growth factor receptor (EGFRt; also known as tEGFR), see reference [36], which is hereby incorporated by reference in its entirety for all purposes, downstream of the CAR. The genes were linked by a T2A ribosomal skip element.

CAR/EGFRt and ffluc/eGFP-encoding lentivirus supernatants were produced in 293T cells co-transfected with each of the lentiviral vector plasmids and the packaging vectors pCHGP-2, pCMV-Rev2 and pCMV-G using Calphos transfection reagent (Clontech, Mountain View, Calif.). Medium was changed 16 h after transfection, and lentivirus collected after 72 h. CAR-T cells were generated as described [35]. In brief, CD8+ or CD4+ bulk T cells were sorted from PBMC of healthy donors, activated with anti-CD3/CD28 beads (Life Technologies), and transduced with lentiviral supernatant. Lentiviral transduction was performed on day 2 by spinoculation, and T cells propagated in RPMI-1640 with 10% human serum, GlutaminMAX (Life technologies), 100 U/mL penicillin-streptomycin and 50 U/mL IL-2. Trypan blue staining was performed to quantify viable T cells. After expansion, EGFRt+ T cells were enriched and expanded by polyclonal stimulation with the CD3-specific Okt3 antibody and irradiated allogeneic PBMC and EBV-LCL feeder cells.

Cytotoxicity, Cytokine Secretion, and CFSE Proliferation Assays

Target cells stably expressing firefly luciferase were incubated in triplicate at $5 \times 10^3$ cells/well with effector T cells at various effector to target (E:T) ratios. After a four-hour incubation luciferin substrate was added to the co-culture and the decrease in luminescence signal in wells that contained target cells and T cells, compared to target cells alone, measured using a luminometer (Tecan). Specific lysis was calculated using the standard formula. For analysis of cytokine secretion, $5 \times 10^4$ T cells were plated in triplicate wells with target cells at a ratio of 4:1 and IFN-γ, TNF-α, and IL-2 measured by ELISA (Biolegend) in supernatant removed after a 24-hour incubation. For analysis of proliferation, $5 \times 10^4$ T cells were labeled with 0.2 μM carboxyfluorescein succinimidyl ester (CFSE, Invitrogen), washed and plated in triplicate wells with target cells at a ratio of 4:1 in CTL medium without exogenous cytokines. After 72 h of incubation, cells were labeled with anti-CD3 or anti-CD4 or anti-CD8 mAb and 7-AAD to exclude dead cells from analysis. Samples were analyzed by flow cytometry and cell division of live T cells assessed by CFSE dilution. The division index was calculated using FlowJo software.

Results

Generation, Detection and Enrichment of Humanized ROR1 CAR T Cells

PBMCs from healthy donors were isolated by Ficoll-Hypaque density gradient centrifugation and bulk CD4+ or CD8+ human T cells were extracted from this cell population using MACS. Directly after isolation the T cells were activated with CD3/28 Dynabeads for two days and then transduced by spinoculation with lentiviral vectors encoding non-humanized or humanized versions of the ROR1-specific CARs at a multiplicity of infection (MOI) of 5. The Dynabeads were removed 4 days after transduction and at day 10 the T cells were enriched for EGFRt-positive cells by labeling with a biotinylated monoclonal αEGFR antibody and MACS with anti-biotin microbeads. After the enrichment, the EGFRt-positive fraction reproducibly accounted for over 90% of total cells except for the hR11 CAR that usually showed a slightly lower percentage of EGFRt-positive cells (FIGS. 4A and 4B).

Cytolytic Activity of Humanized ROR1 CAR T Cells

Figure 5A:
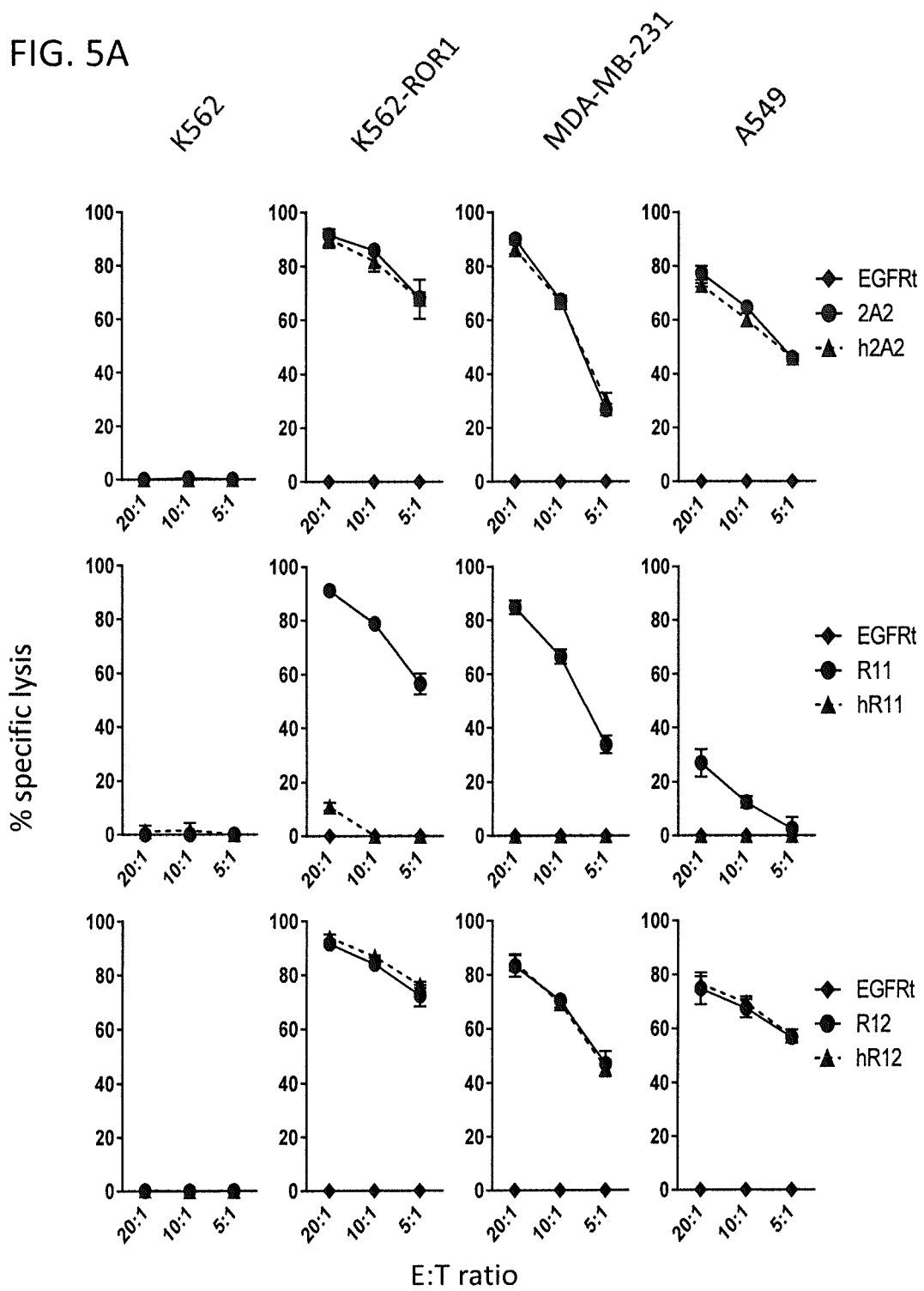
FIG. 5: Cytolytic activity of hROR1 CAR-expressing T cells
  (A) Cytolytic activity of primary human $CD8^+$ T cells expressing the indicated non-humanized or humanized ROR1-specific CARs against ROR1-positive target cells. K562 is a ROR1-negative human leukemia cell line that was used as negative control. K562-ROR1 originates from the same cell line but has been engineered to stably express ROR1. MDA-MB-231 and A549 are human breast and lung cancer cell lines that endogenously express ROR1. All target cell lines were engineered to stably express a firefly (*P. pyralis*) luciferase. The specific lysis of the target cells was calculated based on the intensity of the luminescence signal after addition of Luciferin to a final concentration of 150 µg/ml.
  (B) Summary of the cytolytic activity of human T cells expressing a non-humanized or humanized ROR1-specific CAR against two ROR1 positive target cells lines K562-ROR1 and MDA-MB-231. The data was collected from n=3 independent experiments. The specific lysis was calculated based on the luminesce intensity of ffluc-positive target cells after 6 h incubation with an E:T ratio of 10:1.

CAR T cells were generated as described above and their cytolytic activity was assessed in 6 h cytotoxicity assays against the ROR1-positive and ffluc-expressing target cell lines K562-ROR1, MDA-MB-231 and A549 (FIG. 5A). No specific lysis was detected against ROR1-negative K562 controls. The T cells expressing the h2A2 and hR12 CARs exhibited a very potent anti-tumor effect with a high degree of target cell lysis that was dose dependent, with higher E:T ratios causing higher percentages of target cell lysis. A T cell line transduced with a vector control encoding for the EGFRt transduction marker but not for a CAR caused no lysis of any of the target cells. This demonstrates that the CAR itself induced the target cell lysis and also that CAR-independent target cells lysis, that could in principle occur due to allo-recognition by endogenous TCRs, was not detectable in our experiments. In contrast to the h2A2 and hR12 CARs the hR11 CAR was markedly impaired in its cytolytic activity and showed no detectable lysis in the 6 h assay. Notably it caused detectable and specific target cell lysis if the incubation time was increased to e.g. 24 h.

Figure 5B:
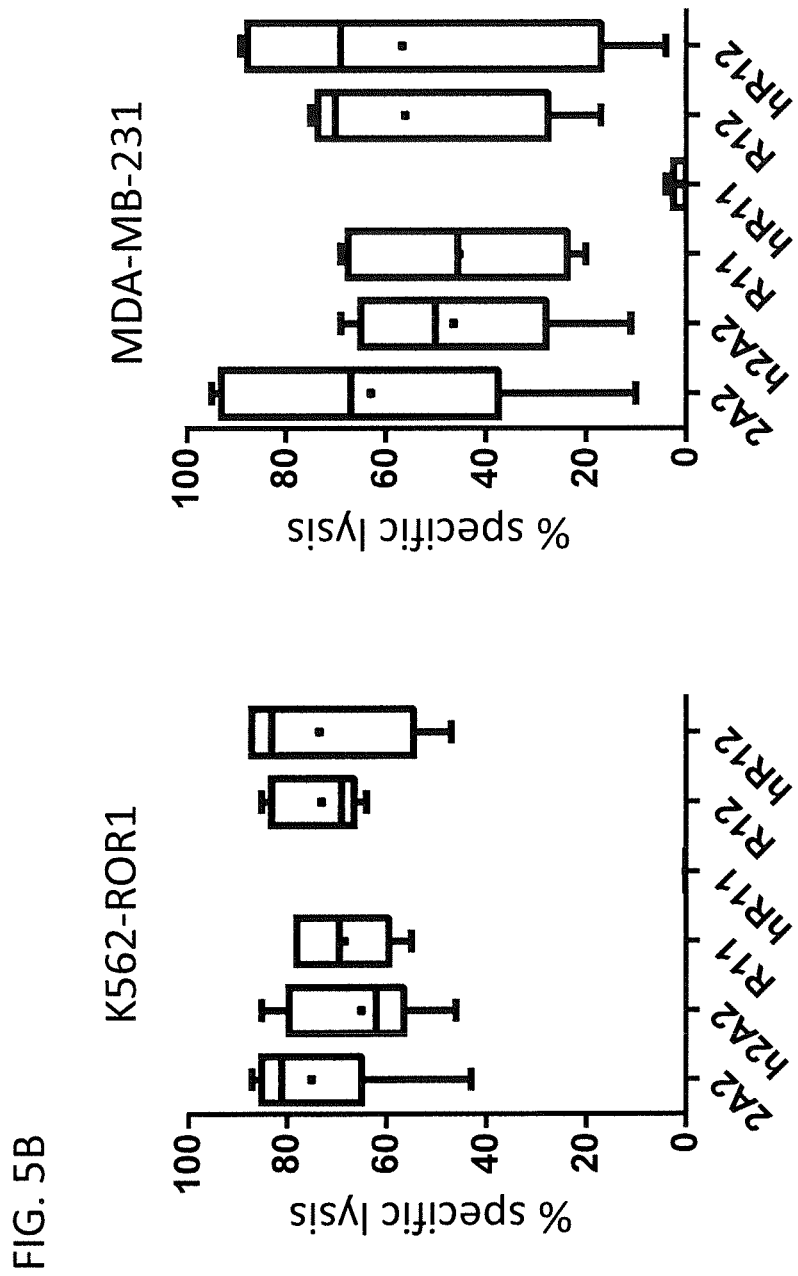

The cytotoxicity assay was repeated under the same conditions with CAR T cells that were generated from n=3 unrelated healthy donors and the ROR1-positive target cells K562-ROR1 and MDA-MB-231 (FIG. 5B). For all donors the lysis observed for the h2A2 and hR12 CARs was consistently strong while the lysis mediated by the hR11 CAR was barely detectable after 6 h incubation time.

Effector Cytokine Secretion Following ROR1-Specific Activation of hROR1 CART Cells CD4+ or CD8+ CAR T cells were generated as described above and co-cultured with lethally irradiated ROR1-expressing target cell lines at an E:T ratio of 4:1 for 24 h. After the incubation the cell culture supernatant was collected and analyzed for the presence of the effector cytokines IL-2 and IFN-γ by ELISA. As controls, the cells were co-cultured with ROR1-negative K562 cells or in absence of any target cell (media control). For controlling the general ability of the CAR T cells to produce the effector cytokines of interest the cells were polyclonally stimulated with a combination of the protein kinase C (PKC)/NF-κB-activator phorbol 12-Myristate 13-Acetate (PMA) and the $Ca^{2+}$ ionopohre ionomycin. The assay procedure was repeated for up to n=3 unrelated healthy T cells donors and the measured cytokine concentrations were used for group analysis.

Figure 6A:
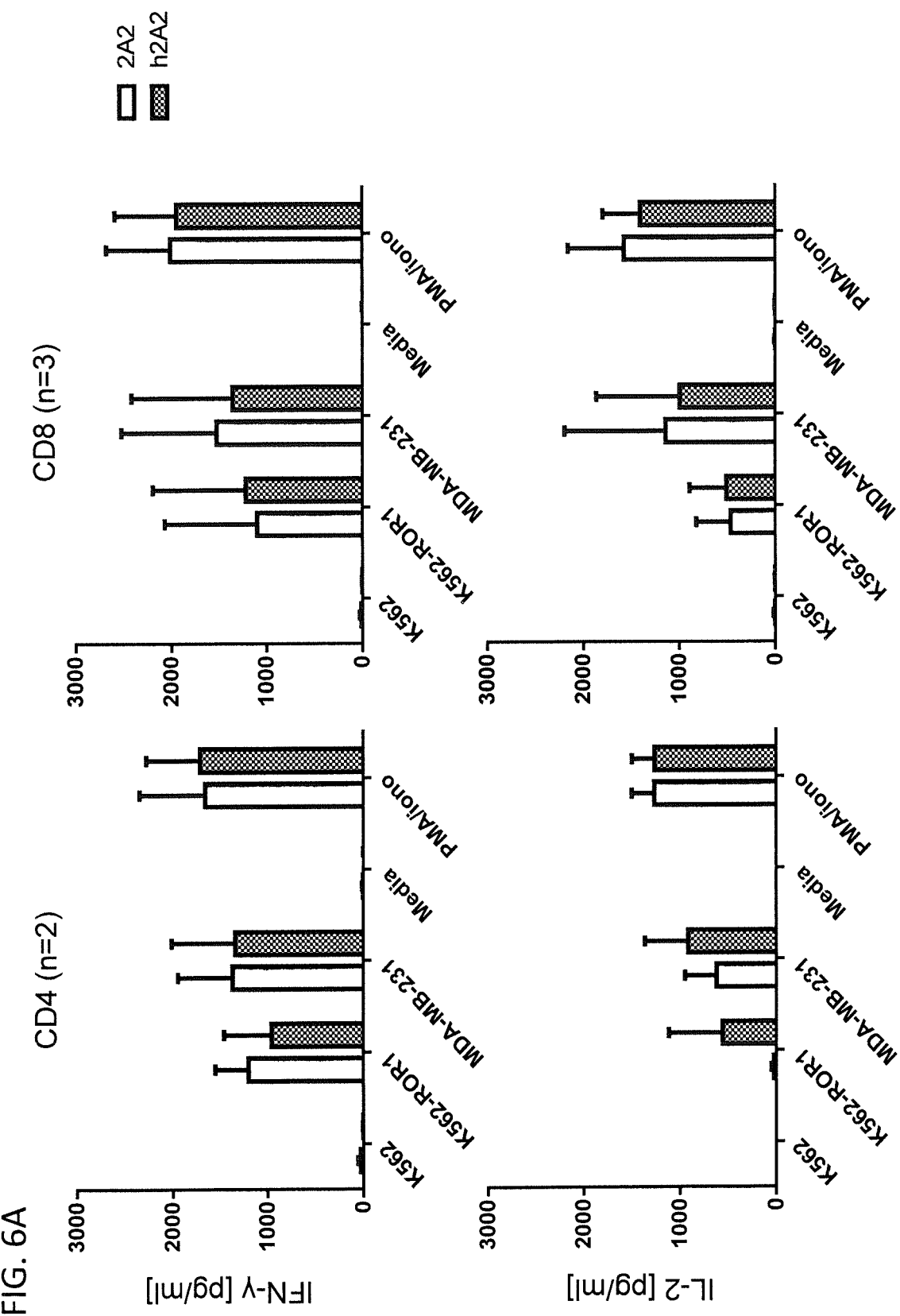
FIG. 6: Cytokine secretion of hROR1 CAR-expressing T cells $CD4^+$ or $CD8^+$ CAR T cells expressing a non-humanized or humanized ROR-specific CAR were co-cultured with lethally irradiated ROR1-positive target cells at an E:T ratio of 4:1. Concentrations of the effector cytokines IL-2 and IFN-γ were measured by ELISA in the cell culture supernatants after 24 h co-culture.
  (A) Comparison of cytokine secretion from 2A2 and h2A2 CAR T cells
  (B) Comparison of cytokine secretion from R11 and hR11 CAR T cells
  (C) Comparison of cytokine secretion from R12 and hR12 CAR T cells

The humanized 2A2 CAR showed a cytokine profile of that was comparable to the non-humanized 2A2 CAR (FIG. 6A). IFN-γ was detected exclusively in samples that included ROR1-positive targets or PMA/Iono and the average concentrations were in the range of 1000-1500 pg/ml for both $CD4^+$ and $CD8^+$ CAR T cells. IL-2 was also exclusively detected in samples that included ROR1-positive target cells and the average concentrations were in the range of 500-1000 pg/ml for $CD4^+$ and $CD8^+$ CAR T cells. Surprisingly, the IL-2 secretion of the h2A2 CAR T cells was elevated in comparison to the non-humanized variant for K562-ROR1 targets.

Figure 6B:
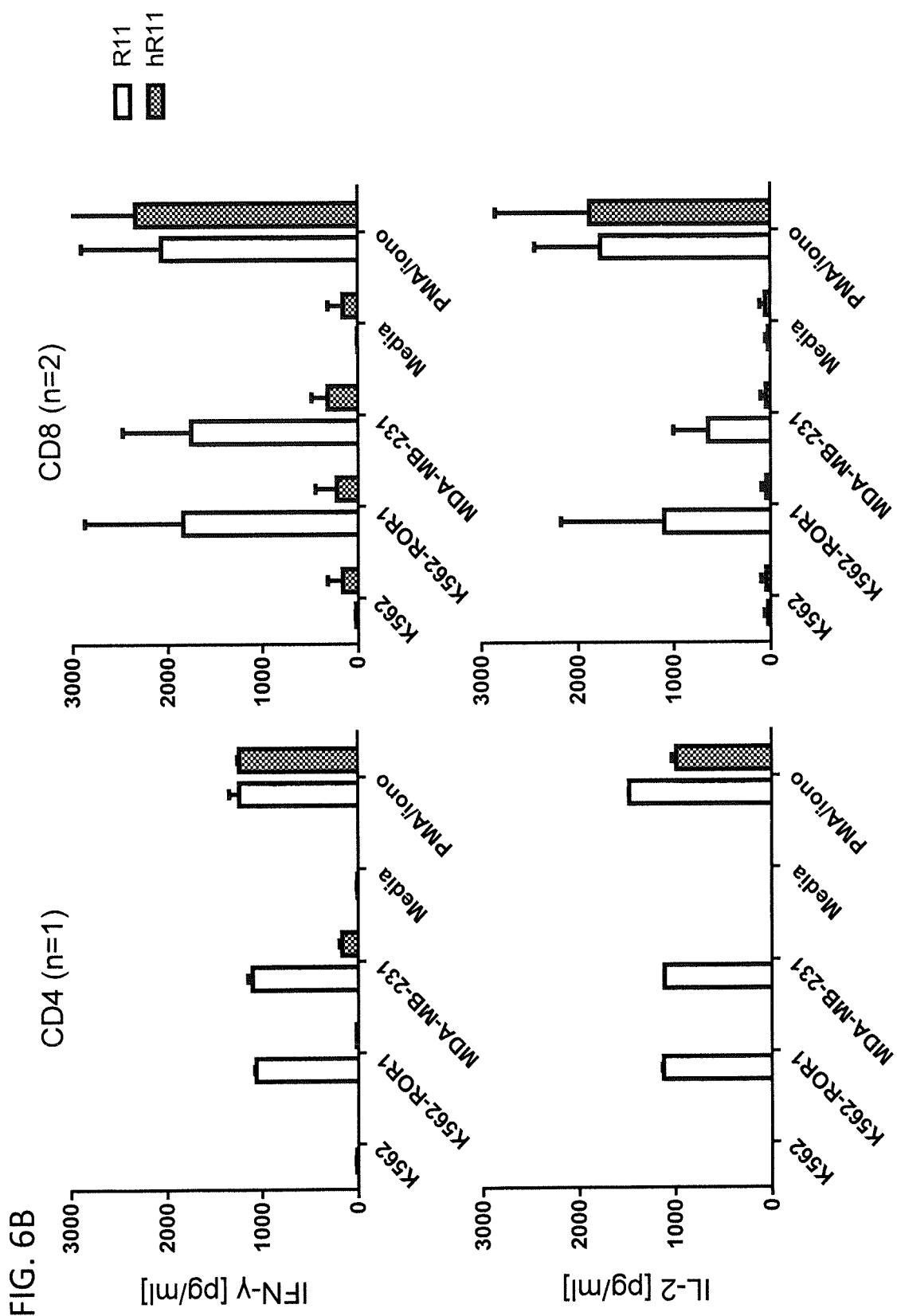

The humanized R11 CAR showed an impaired cytokine secretion as compared to the non-humanized R11 CAR (FIG. 6B). The concentrations of IFN-γ and IL-2 were at background level for the hR11 CAR even in the presence of ROR1-positive target cells while for the non-humanized R11 CAR average concentrations of IFN-γ in the range of 1000 pg/ml for $CD4^+$ T cells and 1800 pg/ml for $CD8^+$ T cells as well as average IL-2 concentrations ranging from 500-1000 pg/ml were detected. Both CAR T cells lines, either expressing the non-humanized or the humanized R11 CAR, retained the general ability to produce IFN-γ and IL-2 in response to the antigen-unspecific stimulation with PMA/Iono.

Figure 6C:
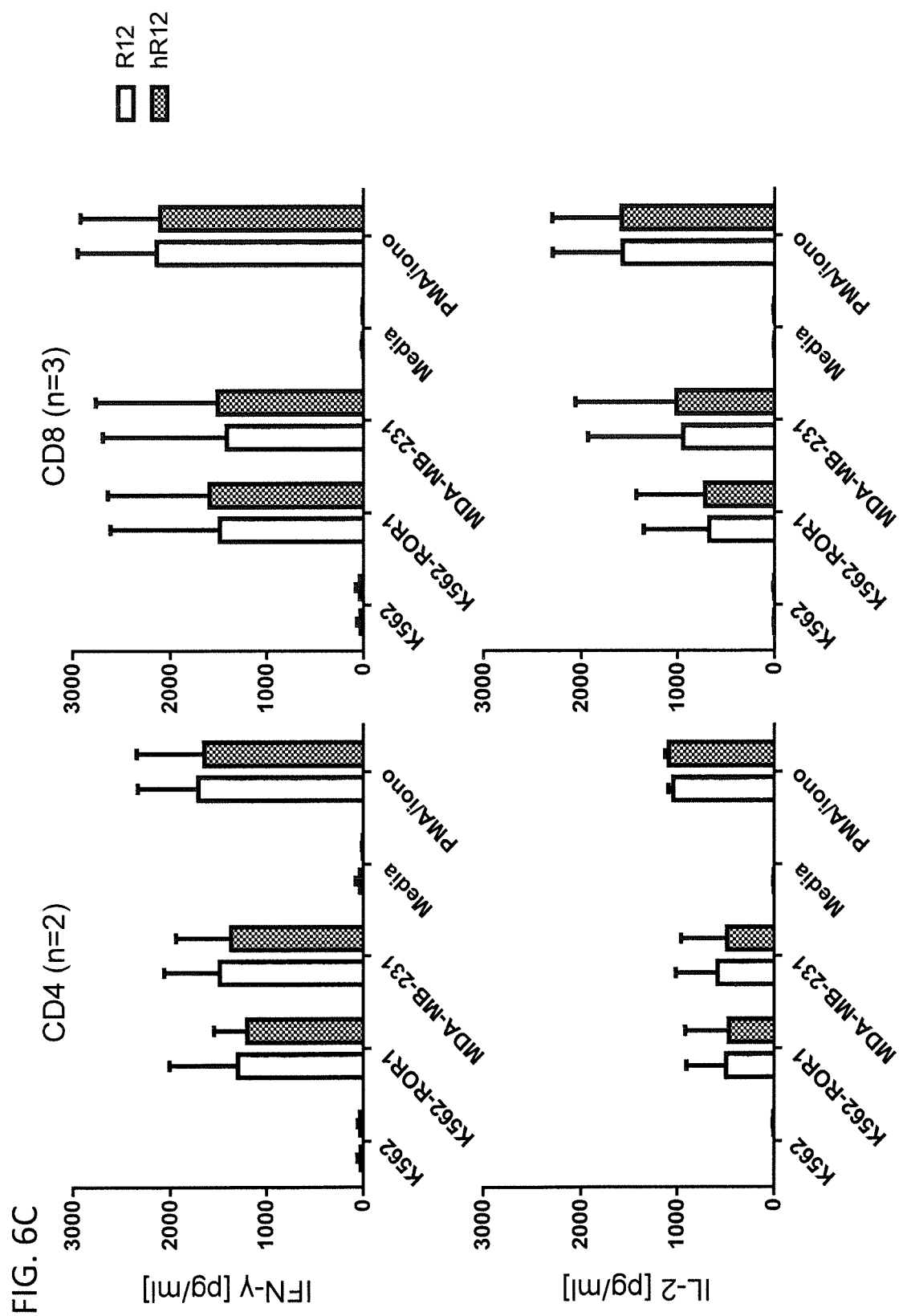

The humanized R12 CAR showed a cytokine profile of that was comparable to the non-humanized R12 CAR (FIG. 6C). IFN-γ was detected exclusively in samples that included ROR1-spositive targets or PMA/Iono and the average concentrations were in the range of 1000-1500 pg/ml for both $CD4^+$ and $CD8^+$ CAR T cells. IL-2 was also exclusively detected in samples that included ROR1-positive target cells and the average concentrations were in the range of 400 pg/ml for $CD4^+$ and 500-800 pg/ml for $CD8^+$ CAR T cells.

Taken together these results demonstrate that the humanization of the targeting domains of the h2A2 and the hR12 CAR did not diminish the potential of $CD4^+$ and $CD8^+$ human T cells expressing these CARs to secrete the effector cytokines IFN-γ and IL-2 after encounter of ROR1-positive target cells. The cytokine levels detected were comparable to and in one instance higher than for the non-humanized CARs. The hR11 CAR, in contrast, mediated no detectable secretion of effector cytokines as response to ROR1-positive target cells even though the T cells retained the general ability for the secretion of both cytokines suggesting that the humanization of the hR11 targeting domain was causative for the observed loss of function. These data are evidence for the fact that the use of humanized binding domains in CARs generated by CDR grafting and only marginally decreasing the affinity of the humanized anti-ROR1 antibodies, see reference [31], cannot predict the functionality of CAR T cells comprising said humanized binding domains in comparison to CAR T cells comprising the non-humanized parental binding domains.

Proliferation of Humanized ROR1 CAR T Cells $CD4^+$ or $CD8^+$ CAR T cells were generated as described, labeled with CFSE and co-cultured with lethally irradiated ROR1-expressing target cell lines at an E:T ratio of 4:1 for 72 h in the absence of exogenous cytokines. After the incubation time the T cells were collected and analyzed for CFSE dilution by flow cytometry. As a negative control, the CAR T cells were cocultured with ROR1-negative K562 cells and as a positive control in the presence of 50 Ul/ml IL-2.

ROR1-negative K562 caused no proliferation of T cells expressing any of the CAR constructs. T cells expressing a vector construct encoding the EGFRt transduction marker but lacking a CAR sequence showed no proliferation in response to any of the target cells above background proliferation (FIG. 7A-D). This demonstrates that the detected proliferation of the ROR1 CAR-T cells was mediated specifically by the CAR as a response to stimulation by ROR1-expressing cells.

Figure 7A:
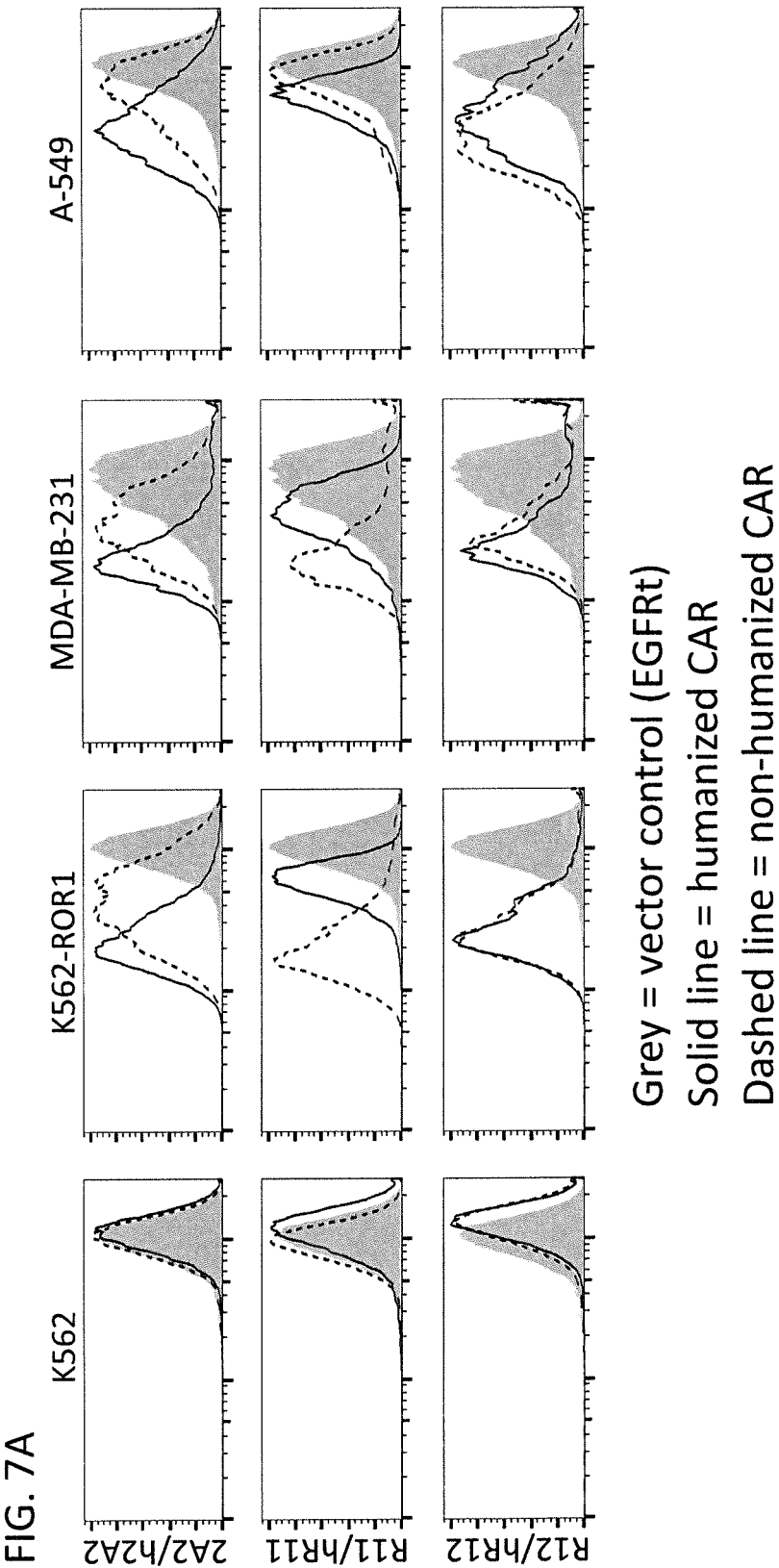
FIG. 7: Proliferation of hROR1 CAR-expressing T cells
  Proliferation of $CD4^+$ ROR1-specific CAR T cells after stimulation with ROR1-positive target cells at an E:T ratio of 4:1. No exogenous cytokines were added to the culture media and the T cell proliferation was assessed by CFSE dye dilution 72 h after stimulation. For analysis, triplicate wells were pooled and the proliferation of live $7AAD^-$, CD4+ T cells was analyzed.
  (A) CFSE flow cytometry histograms of ROR1 CAR T cells with humanized (solid line) or non-humanized (dashed line). Grey filled curves are from vector control T cells (EGFRt).
  (B) Division indices of indicated ROR1 CAR T cells
  (C) Table that summarized the percentages of T cells that went through 0, 1, 2, 3, 4, and 5 cell division cycles.
Figure 7B:
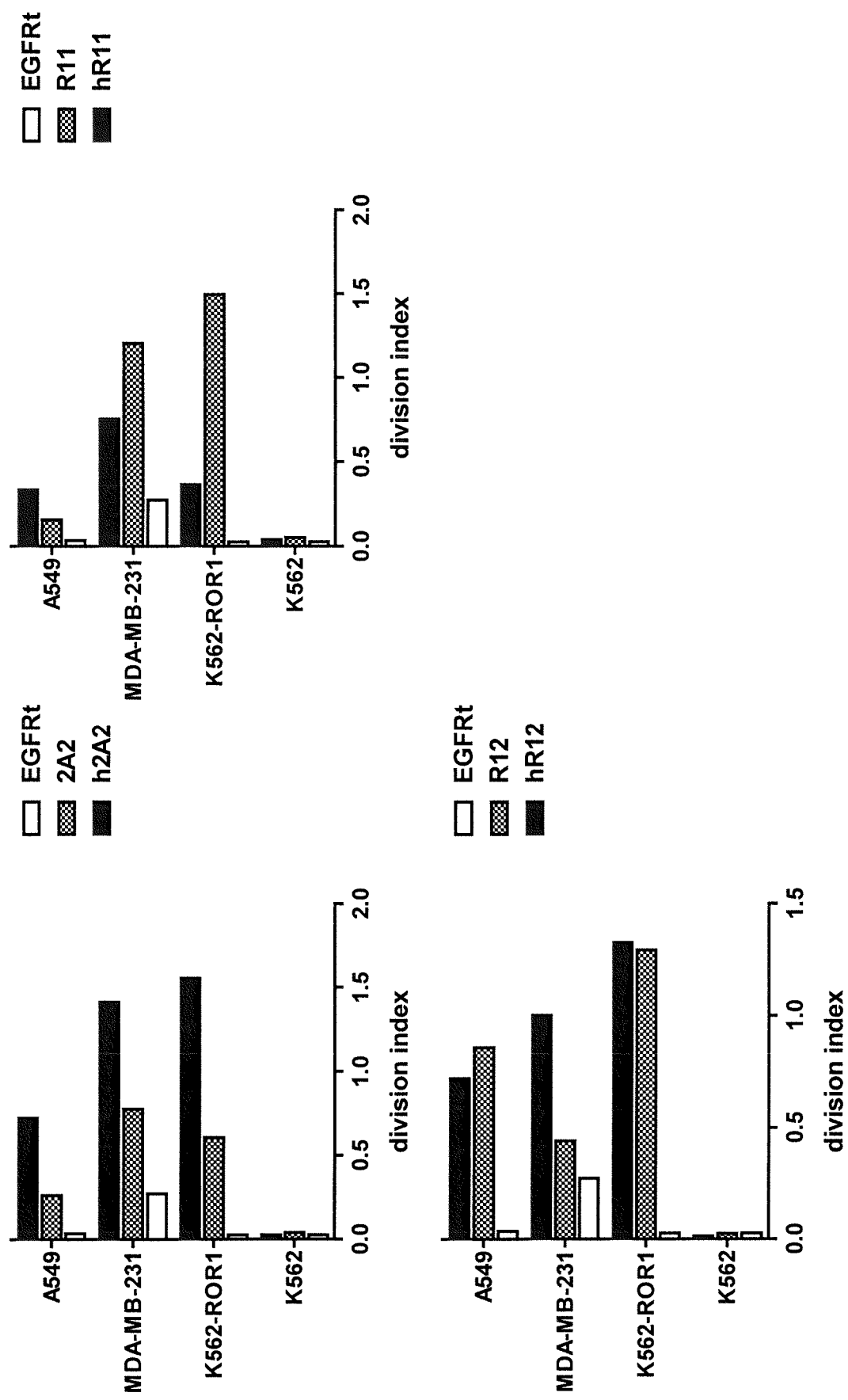

Surprisingly, despite similar cytokine secretion profiles, as determined above, T cells expressing the humanized 2A2 CAR proliferated significantly stronger than T cells expressing the non-humanized 2A2 CAR in response to ROR1-positive target cells (FIG. 7A). Depending on the target cell line, the division indices of the $CD4^+$ h2A2 CAR T cells were consistently 2-3 fold higher as compared to the non-humanized 2A2 ROR1 CAR (FIG. 7B). T cells expressing the humanized 2A2 CAR went through a higher number of cell divisions than T cells expressing the non-humanized 2A2 CAR (FIG. 7C). 60% of the h2A2 CAR T cells with MDA-MB-231 target cells went through three or more cell division cycles, for the non-humanized 2A2 CAR this fraction was 20%. Similarly, 51% of the h2A2 CAR T cells with K562-ROR1 target cells went through three or more cell division cycles, for the non-humanized 2A2 CAR this fraction was 18%. In line with the previous observations, 18% of the h2A2 CAR T cells with A549 target cells went through three or more cell division cycles, for the non-humanized 2A2 CAR this fraction was 5%.

T cells expressing the humanized R11 showed a weaker proliferation than T cells expressing the non-humanized R11 CAR but the proliferation was clearly above background level (FIG. 7A). Depending on the target cells, the division indices were reduced by a factor of 1.5-3.5.

The proliferation of T cells expressing the humanized R12 CAR was specific and overall comparable to T cells expressing the non-humanized variant. Significantly higher proliferation levels were detected for T cells expressing the humanized R12 CAR as compared to the non-humanized variant response to MDA-MB-231. The proliferation index was about 2-fold increased as compared to the non-humanized R12 CAR variant. The percentage of T cells that went through 3 or more cell divisions was 37% for the humanized R12 CAR and 20% for the non-humanized R12 CAR.

Taken together these results demonstrate that the humanized variants of the 2A2 and R12 CARs are capable of activating T cell proliferation in response to antigen encounter at a substantially higher level than the non-humanized variants. The humanized R11 on the other hand had a pronounced decrease in proliferative capacity and the proliferation levels were markedly lowered as compared to the non-humanized R11 CAR.

Example 2

Binding of ROR1-Protein by Humanized ROR1 CARs

Materials and Methods:
Human Subjects

Blood samples were obtained from healthy donors who provided written informed consent to participate in research protocols approved by the Institutional Review Board of the University of Würzburg (Universitätsklinikum Würzburg, UKW). Peripheral blood mononuclear cells (PBMC) were isolated by centrifugation over Ficoll-Hypaque (Sigma, St. Louis, Mo.).

Immunophenotyping

PBMC and T cell lines were stained with one or more of the following conjugated mAb: CD3, CD4, CD8 and matched isotype controls (BD Biosciences, San Jose, Calif.). Transduced T cell lines were stained with biotin-conjugated anti-EGFR antibody (ImClone Systems Incorporated, Branchburg, N.J.) and streptavidin-PE (BD Biosciences, San Jose, Calif.). Staining with 7-AAD (BD Biosciences) was performed for live/dead cell discrimination as directed by the manufacturer. Flow analyses were done on a FACSCanto and data analyzed using FlowJo software (Treestar, Ashland, Oreg.).

Lentiviral Vector Construction, Preparation of Lentivirus, and Generation of CAR-T Cells The construction of epHIV7 lentiviral vectors containing ROR1-specific CARs with a short or long spacer and a 4-1BB costimulatory domain has been described, see reference [35], which is hereby incorporated by reference in its entirety for all purposes. All CAR constructs encoded a truncated epidermal growth factor receptor (EGFRt; also known as tEGFR), see reference [36], which is hereby incorporated by reference in its entirety for all purposes, downstream of the CAR. The genes were linked by a T2A ribosomal skip element.

CAR/EGFRt and ffluc/eGFP-encoding lentivirus supernatants were produced in 293T cells co-transfected with each of the lentiviral vector plasmids and the packaging vectors pCHGP-2, pCMV-Rev2 and pCMV-G using Calphos transfection reagent (Clontech, Mountain View, Calif.). Medium was changed 16 h after transfection, and lentivirus collected after 72 h. CAR-T cells were generated as described [35]. In brief, CD8$^+$ or CD4$^+$ bulk T cells were sorted from PBMC of healthy donors, activated with anti-CD3/CD28 beads (Life Technologies), and transduced with lentiviral supernatant. Lentiviral transduction was performed on day 2 by spinoculation, and T cells propagated in RPMI-1640 with 10% human serum, GlutaminMAX (ThermoFisher Scientific, MA), 100 U/mL penicillin-streptomycin and 50 U/mL IL-2. Trypan blue staining was performed to quantify viable T cells. After expansion, EGFRt$^+$ T cells were enriched and expanded by polyclonal stimulation with the CD3-specific Okt3 antibody and irradiated allogeneic PBMC and EBV-LCL feeder cells.

Binding of ROR1

Recombinant aggregated ROR1 protein was labeled with the AlexaFluor647 labeling kit (ThermoFisher Scientific, MA) and used to stain T cells expressing ROR1 CARs. The T cells were washed once in PBS, 0.25% FCS and then resuspended in the same buffer containing a final concentration of 5.3 µg/ml labeled ROR1 protein and monoclonal αEGFRt antibody. After an incubation time of 15 min the cells were washed with an excess of PBS, 0.25% FCS and analyzed by flow cytometry.

Figure 8:
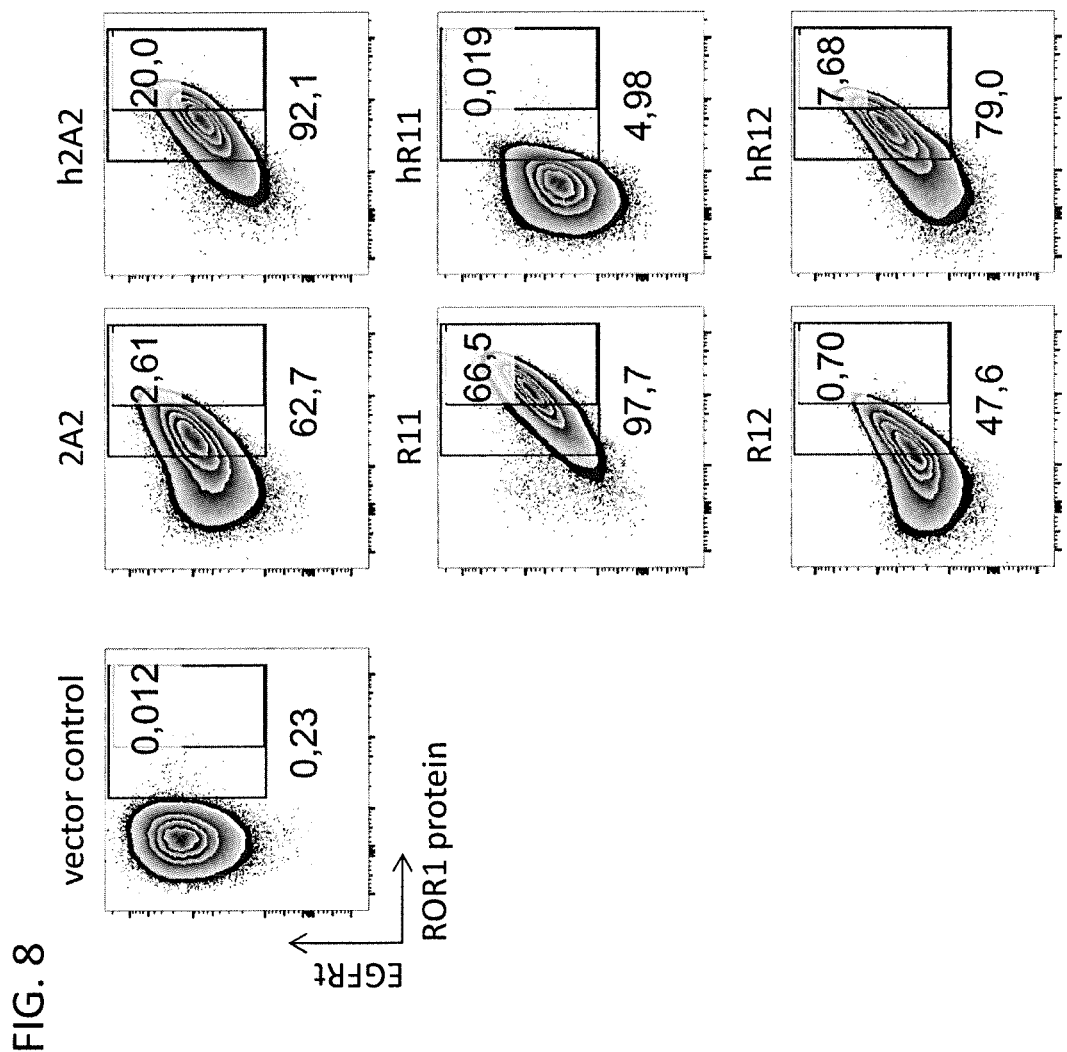
FIG. 8: Binding of ROR1 protein by hROR1 CAR T cells
  Human $CD8^+$ T cells expressing non-humanized or humanized ROR1 CARs were collected, washed with PBS, 0.25% FCS and then incubated 10 min in the same buffer containing a final concentration of 5.3 µ/ml AlexaFluor 647-labeled aggregated ROR1 protein and monoclonal αEGFR antibody. Afterwards the cells were washed with PBS, 0.25% FCS and analyzed by flow cytometry.

Results:

Compared to their non-humanized counterparts the humanized 2A2 and R12 ROR1 CARs showed significantly stronger binding to the ROR1 protein (FIG. 8). A higher overall percentage of ROR1 protein binding was detected, suggesting a better surface availability and/or binding capability of the humanized CARs. The percentage of T cells with a distinct AlexaFluor647 signal was 62.7% for the non-humanized and 92.1% for the humanized 2A2 CAR. Similarly, the percentage of T cells with a distinct AlexaFluor647 signal was 47.6% for the non-humanized and 79.0% for the humanized R12 CAR.

Further, the percentage of CAR T cells that showed strong ROR1 binding was increased for the humanized 2A2 and R12 CARs and consequently a lesser frequency of weak ROR1-binding was detected for these samples. The percentage of T cells with high AlexaFluor647 signal was 2.61% for the non-humanized and 20.0% for the humanized 2A2 CAR. Similarly, the percentage of T cells with high AlexaFluor647 signal was 0.7% for the non-humanized and 7.68% for the humanized R12 CAR. This accounts for a roughly 10-fold increase in the number of T cells that strongly bind to the ROR1 protein.

The humanized R11 showed low overall ROR1 protein binding with 4.98% of AlexaFluor647-positive T cells as compared to 97.9% for the non-humanized R11 CAR. Similarly, the frequency of T cells with high AlexaFluor647 signal was 0.019% for the humanized R11 and 66.5% for the non-humanized variant.

In summary these data demonstrate that the humanized versions of the 2A2 and the R12 CAR have a stronger binding to the ROR1 antigen than the non-humanized versions. That was unexpected and may provide an explanation for the elevated activity in parts of the assays that were performed for example 1.

Example 3

Regression of Human Jeko-1 Mantle Cell Lymphoma in NOD/SCID/γc−/− (NSG) Mice after Adoptive Immunotherapy with CAR-T Cells Expressing Humanized ROR1 CARs Materials and Methods:
Human Subjects Blood samples were obtained from healthy donors who provided written informed consent to participate in research protocols approved by the Institutional Review Board of the University of Würzburg (Universitätsklinikum Würzburg, UKW). Peripheral blood mononuclear cells (PBMC) were isolated by centrifugation over Ficoll-Hypaque (Sigma, St. Louis, Mo.).

Cell Lines

The JeKo-1 (wild type), 293T, K562, MDA-MB-231 and A549 cell lines were obtained from the American Type Culture Collection. K562-ROR1 were generated by lentiviral transduction with the full-length ROR1-gene. Luciferase expressing lines were derived by lentiviral transduction of the above mentioned cell lines with the firefly (P. pyralis) luciferase (ffluc)-gene. The cells were cultured in Dulbecco's modified Eagle's medium supplemented with 10% fetal calf serum and 100 U/ml penicillin/streptomycin.

Immunophenotyping

PBMC and T cell lines were stained with one or more of the following conjugated mAb: CD3, CD4, CD8 and matched isotype controls (BD Biosciences, San Jose, Calif.). Transduced T cell lines were stained with biotin-conjugated anti-EGFR antibody (ImClone Systems Incorporated, Branchburg, N.J.) and streptavidin-PE (BD Biosciences, San Jose, Calif.). Staining with 7-AAD (BD Biosciences) was performed for live/dead cell discrimination as directed by the manufacturer. Flow analyses were done on a FACSCanto and data analyzed using FlowJo software (Treestar, Ashland, Oreg.).

Lentiviral Vector Construction, Preparation of Lentivirus, and Generation of CAR-T Cells and JeKo-1/ffluc Cells The construction of epHIV7 lentiviral vectors containing ROR1-specific CARs with a short or long spacer and a 4-1BB costimulatory domain has been described, see reference [35], which is hereby incorporated by reference in its entirety for all purposes. All CAR constructs encoded a truncated epidermal growth factor receptor (EGFRt; also known as tEGFR), see reference [36], which is hereby incorporated by reference in its entirety for all purposes, downstream of the CAR. The genes were linked by a T2A ribosomal skip element.

CAR/EGFRt and ffluc/eGFP-encoding lentivirus supernatants were produced in 293T cells co-transfected with each of the lentiviral vector plasmids and the packaging vectors pCHGP-2, pCMV-Rev2 and pCMV-G using Calphos transfection reagent (Clontech, Mountain View, Calif.). Medium was changed 16 h after transfection, and lentivirus collected after 72 h. CAR-T cells were generated as described [35]. In brief, $CD8^+$ or $CD4^+$ bulk T cells were sorted from PBMC of healthy donors, activated with anti-CD3/CD28 beads (Life Technologies), and transduced with lentiviral supernatant. Lentiviral transduction was performed on day 2 by spinoculation, and T cells propagated in RPMI-1640 with 10% human serum, GlutaminMAX (Life technologies), 100 U/mL penicillin-streptomycin and 50 U/mL IL-2. Trypan blue staining was performed to quantify viable T cells. After expansion, $EGFRt^+$ T cells were enriched and expanded by polyclonal stimulation with the CD3-specific Okt3 antibody and irradiated allogeneic PBMC and EBV-LCL feeder cells. JeKo-1/ffluc cells were generated by lentiviral transduction with the ffluc/eGFP-encoding lentivirus.

Cytotoxicity, Cytokine Secretion, and CFSE Proliferation Assays

Target cells stably expressing firefly luciferase were incubated in triplicate at $5 \times 10^3$ cells/well with effector T cells at various effector to target (E:T) ratios. After a four-hour incubation luciferin substrate was added to the co-culture and the decrease in luminescence signal in wells that contained target cells and T cells, compared to target cells alone, measured using a luminometer (Tecan). Specific lysis was calculated using the standard formula. For analysis of cytokine secretion, $5 \times 10^4$ T cells were plated in triplicate wells with target cells at a ratio of 4:1 and IFN-γ, TNF-α, and IL-2 measured by ELISA (Biolegend) in supernatant removed after a 24-hour incubation. For analysis of proliferation, $5 \times 10^4$ T cells were labeled with 0.2 µM carboxyfluorescein succinimidyl ester (CFSE, Invitrogen), washed and plated in triplicate wells with target cells at a ratio of 4:1 in CTL medium without exogenous cytokines. After 72 h of incubation, cells were labeled with anti-CD3 or anti-CD4 or anti-CD8 mAb and 7-AAD to exclude dead cells from analysis. Samples were analyzed by flow cytometry and cell division of live T cells assessed by CFSE dilution. The division index was calculated using FlowJo software.

Experiments in NOD/SCID/γc-/- (NSG) Mice

The Institutional Animal Care and Use Committee approved all mouse experiments. Six- to 8-week old female NOD.Cg-Prkdcscid Il2rgtm1Wjl/SzJ (NSG) mice were obtained from the Jackson Laboratory or bred in-house. Mice were injected with $0.5 \times 10^6$ JeKo-1/ffluc tumor cells via tail vein and received a subsequent tail vein injection of h2A2 or hR12 ROR1 CAR cells. Both ROR1 CAR T cell lines (h2A2 and hR12) expressed the transduction marker EGFRt. Control T cells expressed only the EGFRt transduction marker.

For bioluminescence imaging of tumor growth, mice received intraperitoneal injections of luciferin substrate (Caliper Life Sciences) resuspended in PBS (15 µg/g body weight). Mice were anesthetized with isoflurane and imaged using an Xenogen IVIS Imaging System (Caliper) 10 minutes after luciferin injection in small binning mode at an acquisition time of 1 s to 1 min to obtain unsaturated images. Luciferase activity was analyzed using Living Image Software (Caliper). The photon flux (radiance) was measured within regions of interest that encompassed the entire body of each individual mouse.

Results:

To assess the in vivo activity of humanized ROR1 CARs, we inoculated cohorts (n=5) of immunodeficient NSG mice with the human, ROR1-expressing mantle cell lymphoma line JeKo-1/ffluc by tail vein injection. 21 days later, when the tumor was disseminated, the mice were treated with a single intravenous dose of hR12 or h2A2 ROR1 CAR T cells. Control mice were treated with T cells only expressing an EGFRt control vector or were left untreated.

Figure 9A:
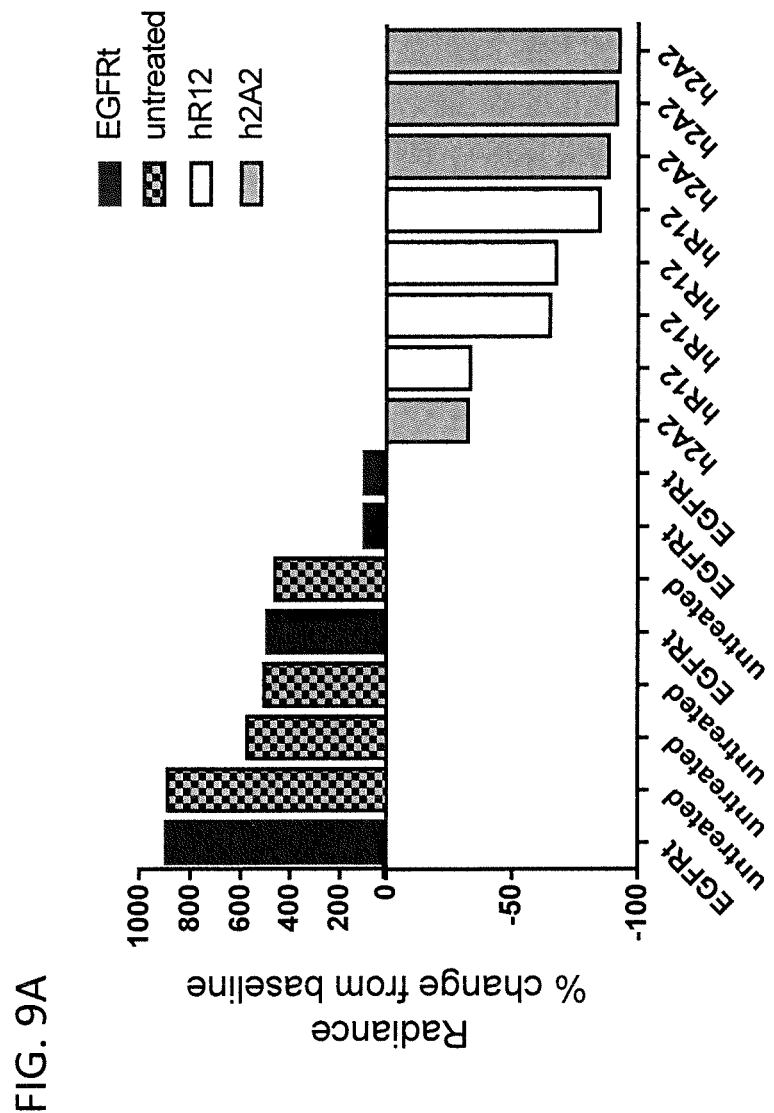
FIG. 9: In vivo activity of hROR1 CAR T cells
  NSG mice were inoculated with ROR1-expressing Jeko-1 mantle cell lymphoma lines and received a treatment of humanized R12 or 2A2 CAR T cells 21 days later.
  (A) Mice were injected with luciferin at day 28 and radiance signals, which are emitted by ffluc-positive tumor cell, were detected. Displayed is the change of average radiance per mouse for the four best responding mice of each group compared to the baseline signals, which were measured on day 21.
  (B) Flow cytometry plots showing the frequency of EGFRt-positive $CD4^+$ and $CD8^+$ T cells after EGFRt in the bone marrow of mice that received hR12 or h2A2 ROR1 CAR T cells at day 56.

We observed rapid tumor regression and improved survival in all of the mice treated with hR12 and h2A2 ROR1 CAR-T cells (response rate 100%). FIG. 9A displays the tumor regression 7 days after T cell transfer as percentage change from baseline radiance. The baseline was measured for each mouse before the treatment on day 21. In contrast to humanized ROR1 CAR-treated mice, the control groups, which were either left untreated or were treated with T cells expressing the EGFRt control vector, showed continued tumor growth in all of the mice (response rate 0%). The average radiance 7 days after CAR T cell treatment was $2*10^4$ p/sec/cm$^2$/sr for hR12 and $1*10^5$ for h2A2. The average radiance of the control groups was $6*10^6$ for untreated mice and $1*10^6$ for mice treated with the EGFRt-only vector control.

Figure 9B:
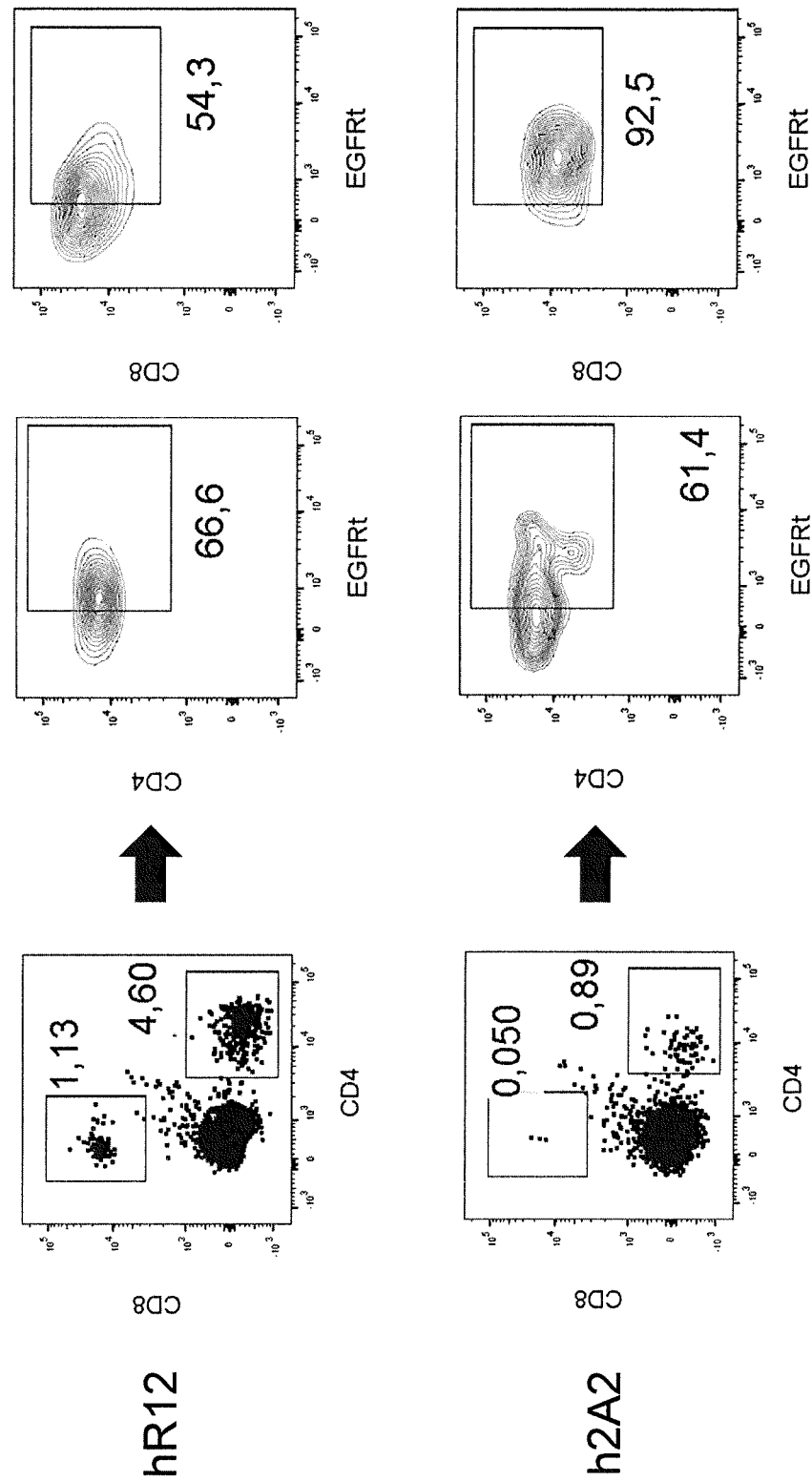

Humanized ROR1 CAR T cells engrafted and persisted in the mice and were detectable in spleen and bone marrow of the mice until the end of the experiment. FIG. 9B shows representative flow cytometry data from bone marrow samples of one mouse from the hR12 cohort and one mouse of the h2A2 cohort at day 56. CD4 and CD8 T cells were detectable, and expressed the humanized ROR1 CAR. We confirmed the presence of humanized ROR1 CAR T cells in organ samples; the proportion of humanized ROR1 CAR T cells in the total cells varied between individual mice but was generally in the range of 1-10%.

In summary, these data demonstrate that the h2A2 and the hR12 CARs conferred a strong and specific anti-tumor activity in vivo.

INDUSTRIAL APPLICABILITY

The CARs, combinations of CARs, the recombinant mammalian cells and the methods and medical uses according to the invention are industrially applicable. For example, they can be used as, or for the production of, pharmaceutical products.

REFERENCES

1. Kalos, M., et al., *T cells with chimeric antigen receptors have potent antitumor effects and can establish memory in patients with advanced leukemia.* Sci Transl Med, 2011. 3(95): p. 95ra73.
2. Kochenderfer, J. N., et al., *B-cell depletion and remissions of malignancy along with cytokine-associated toxicity in a clinical trial of anti-CD19 chimeric-antigen-receptor-transduced T cells.* Blood, 2012. 119(12): p. 2709-20.
3. Kochenderfer, J. N., et al., *Eradication of B-lineage cells and regression of lymphoma in a patient treated with autologous T cells genetically engineered to recognize CD19.* Blood, 2010. 116(20): p. 4099-102.
4. Morgan, R. A., et al., *Cancer regression in patients after transfer of genetically engineered lymphocytes.* Science, 2006. 314(5796): p. 126-9.
5. Porter, D. L., et al., *Chimeric antigen receptor-modified T cells in chronic lymphoid leukemia.* N Engl J Med, 2011. 365(8): p. 725-33.
6. Eshhar, Z., et al., *Specific activation and targeting of cytotoxic lymphocytes through chimeric single chains consisting of antibody-binding domains and the gamma or zeta subunits of the immunoglobulin and T-cell receptors.* Proc Natl Acad Sci USA, 1993. 90(2): p. 720-4.
7. Kershaw, M. H., et al., *Supernatural T cells: genetic modification of T cells for cancer therapy.* Nat Rev Immunol, 2005. 5(12): p. 928-40.
8. Sadelain, M., I. Riviere, and R. Brentjens, *Targeting tumours with genetically enhanced T lymphocytes.* Nat Rev Cancer, 2003. 3(1): p. 35-45.
9. Brentjens, R. J., et al., *Safety and persistence of adoptively transferred autologous CD19-targeted T cells in patients with relapsed or chemotherapy refractory B-cell leukemias.* Blood, 2011. 118(18): p. 4817-28.
10. Hudecek, M., et al., *The B-cell tumor-associated antigen ROR1 can be targeted with T cells modified to express a ROR1-specific chimeric antigen receptor.* Blood, 2010. 116(22): p. 4532-41.
11. Matsuda, T., et al., *Expression of the receptor tyrosine kinase genes, Ror1 and Ror2, during mouse development.* Mech Dev, 2001. 105(1-2): p. 153-6.
12. Rosenwald, A., et al., *Relation of gene expression phenotype to immunoglobulin mutation genotype in B cell chronic lymphocytic leukemia.* J Exp Med, 2001. 194(11): p. 1639-47.
13. Klein, U., et al., *Gene expression profiling of B cell chronic lymphocytic leukemia reveals a homogeneous phenotype related to memory B cells.* J Exp Med, 2001. 194(11): p. 1625-38.
14. Baskar, S., et al., *Unique cell surface expression of receptor tyrosine kinase ROR1 in human B-cell chronic lymphocytic leukemia.* Clin Cancer Res, 2008. 14(2): p. 396-404.
15. Bicocca, V. T., et al., *Crosstalk between ROR1 and the Pre-B cell receptor promotes survival of t(1;19) acute lymphoblastic leukemia.* Cancer Cell, 2012. 22(5): p. 656-67.
16. Daneshmanesh, A. H., et al., *Ror1, a cell surface receptor tyrosine kinase is expressed in chronic lymphocytic leukemia and may serve as a putative target for therapy.* Int J Cancer, 2008. 123(5): p. 1190-5.
17. Fukuda, T., et al., *Antisera induced by infusions of autologous Ad-CD154-leukemia B cells identify ROR1 as an oncofetal antigen and receptor for Wnt5a.* Proc Natl Acad Sci USA, 2008. 105(8): p. 3047-52.
18. Yamaguchi, T., et al., *NKX2-1/TITF1/TTF-1-Induced ROR1 is required to sustain EGFR survival signaling in lung adenocarcinoma.* Cancer Cell, 2012. 21(3): p. 348-61.
19. Zhang, S., et al., *ROR1 is expressed in human breast cancer and associated with enhanced tumor-cell growth.* PLoS One, 2012. 7(3): p. e31127.
20. Zhang, S., et al., *The onco-embryonic antigen ROR1 is expressed by a variety of human cancers.* Am J Pathol, 2012. 181(6): p. 1903-10.
21. Dave, H., et al., *Restricted cell surface expression of receptor tyrosine kinase ROR1 in pediatric B-lineage acute lymphoblastic leukemia suggests targetability with therapeutic monoclonal antibodies.* PLoS One, 2012. 7(12): p. e52655.
22. Gentile, A., et al., *Ror1 is a pseudokinase that is crucial for Met-driven tumorigenesis.* Cancer Res, 2011. 71(8): p. 3132-41.
23. Choudhury, A., et al., *Silencing of ROR1 and FMOD with siRNA results in apoptosis of CLL cells.* Br J Haematol, 2010. 151(4): p. 327-35.
24. Maude, S. L., et al., *Chimeric antigen receptor T cells for sustained remissions in leukemia.* N Engl J Med, 2014. 371(16): p. 1507-17.
25. Grupp, S. A., et al., *Chimeric antigen receptor-modified T cells for acute lymphoid leukemia.* N Engl J Med, 2013. 368(16): p. 1509-18.
26. Davila, M. L., et al., *Efficacy and toxicity management of 19-28z CAR T cell therapy in B cell acute lymphoblastic leukemia.* Sci Transl Med, 2014. 6(224): p. 224ra25.
27. Lamers, C. H., et al., *Treatment of metastatic renal cell carcinoma with CAIX CAR-engineered T cells: clinical evaluation and management of on-target toxicity.* Mol Ther, 2013. 21(4): p. 904-12.
28. Turtle, C. J., et al., *CD19 CAR-T cells of defined CD4+:CD8+ composition in adult B cell ALL patients.* J Clin Invest, 2016. 126(6): p. 2123-38.
29. Maus, M. V., et al., *T cells expressing chimeric antigen receptors can cause anaphylaxis in humans.* Cancer Immunol Res, 2013. 1(1): p. 26-31.
30. Sommermeyer, D., et al., *Fully human CD19-specific chimeric antigen receptors for T-cell therapy.* Leukemia, 2017.
31. Waldmeier, L., et al., *Transpo-mAb display: Transposition-mediated B cell display and functional screening of full-length IgG antibody libraries.* MAbs, 2016. 8(4): p. 726-40.
32. Baca, M., et al., *Antibody humanization using monovalent phage display.* J Biol Chem, 1997. 272(16): p. 10678-84.
33. Altschul, S. F., et al., *Basic local alignment search tool.* J Mol Biol, 1990. 215(3): p. 403-10.
34. Altschul, S. F., et al., *Gapped BLAST and PSI-BLAST: a new generation of protein database search programs.* Nucleic Acids Res, 1997. 25(17): p. 3389-402.
35. Hudecek, M., et al., *Receptor affinity and extracellular domain modifications affect tumor recognition by ROR1-specific chimeric antigen receptor T cells.* Clin Cancer Res, 2013. 19(12): p. 3153-64.
36. Wang, X., et al., *A transgene-encoded cell surface polypeptide for selection, in vivo tracking, and ablation of engineered cells.* Blood, 2011. 118(5): p. 1255-63.
37. Yang, J. et al., Therapeutic potential and challenges of targeting receptor tyrosine kinase ROR1 with monoclonal antibodies in B-cell malignancies. PLoS One. 2011; 6(6): e21018.

The invention claimed is:

1. A receptor tyrosine kinase-like orphan receptor 1 (ROR1)-specific chimeric antigen receptor (CAR) comprising a humanized targeting domain capable of binding to ROR1, wherein the humanized targeting domain comprises:
   a) an antibody heavy chain variable domain amino acid sequence selected from the group consisting of:
      a1) the amino acid sequence of SEQ ID No: 1;
      a2) the amino acid sequence of SEQ ID No: 3; and
      a3) the amino acid sequence of SEQ ID No: 5; and
   b) an antibody light chain variable domain amino acid sequence selected from the group consisting of:
      b1) the amino acid sequence of SEQ ID No: 2;
      b2) the amino acid sequence of SEQ ID No: 4; and
      b3) the amino acid sequence of SEQ ID No: 6.

2. The ROR1-specific CAR according to claim 1, wherein the humanized targeting domain comprises the following sequences in an N- to C-terminal order:
   I) the antibody heavy chain variable domain amino acid sequence of SEQ ID No: 1, an amino acid linker sequence, and the antibody light chain variable domain amino acid sequence of SEQ ID No: 2;
   II) the antibody heavy chain variable domain amino acid sequence of SEQ ID No: 3, an amino acid linker sequence, and the antibody light chain variable domain amino acid sequence of SEQ ID No: 4; or
   III) the antibody heavy chain variable domain amino acid sequence of SEQ ID No: 5, an amino acid linker sequence, and the antibody light chain variable domain amino acid sequence of SEQ ID No: 6.

3. A combination of CARs comprising at least a first and a second CAR, the combination being ROR1-specific, wherein said first and said second CAR are present on different polypeptide chains, and wherein:
   c) said first CAR comprises a first humanized targeting domain comprising an antibody heavy chain variable domain amino acid sequence selected from the group consisting of:
      c1) the amino acid sequence of SEQ ID No: 1;
      c2) the amino acid sequence of SEQ ID No: 3; and
      c3) the amino acid sequence of SEQ ID No: 5; and
   d) said second CAR comprises a second humanized targeting domain comprising an antibody light chain variable domain amino acid sequence selected from the group consisting of:
      d1) the amino acid sequence of SEQ ID No: 2;
      d2) the amino acid sequence of SEQ ID No: 4; and
      d3) the amino acid sequence of SEQ ID No: 6.

4. The ROR1-specific CAR according to claim 1, wherein the CAR further comprises a costimulatory domain capable of mediating costimulation to immune cells.

5. The ROR1-specific CAR according to claim 1, further comprising a transmembrane polypeptide.

6. The ROR1-specific CAR according to claim 1, further comprising a CAR spacer domain.

7. The ROR1-specific CAR according to claim 1, further comprising a suicide gene product that allows the selective killing of CAR T cells.

8. The ROR1-specific CAR according to claim 1, comprising, in an N- to C-terminal order: i) a signal peptide for direction into the endoplasmic reticulum; ii) a humanized targeting domain; iii) the CAR spacer domain; iv) a transmembrane polypeptide; v) a costimulatory domain; vi) a CD3z signaling domain.

9. A polynucleotide encoding the ROR1-specific CAR according to claim 1.

10. A recombinant mammalian cell expressing at least one ROR1-specific CAR according to claim 1.

11. The recombinant mammalian cell according to claim 10, wherein the recombinant mammalian cell is an immune cell.

12. The recombinant mammalian cell according to claim 10, wherein the recombinant mammalian cell is a CD8+ killer T cell, a CD4+ helper T cell, a naive T cell, a memory T cell, a central memory T cell, an effector memory T cell, a memory stem T cell, an invariant T cell, an NKT cell, a cytokine induced killer T cell, a g/d T cell, a natural killer cell, a monocyte, a macrophage, a dendritic cell, or a granulocyte.

13. A method for producing a recombinant mammalian cell according to claim 10, the method comprising the steps of:
   (a) providing a mammalian cell;
   (b) introducing into said mammalian cell of step (a) at least one polynucleotide encoding said at least one ROR1-specific CAR or said combination of CARs; and (c) expressing said at least one ROR1-specific CAR or said combination of CARs from said at least one polynucleotide in said cell;

thereby obtaining said recombinant mammalian cell.

14. A method for treating a patient having a ROR1-positive cancer, comprising administering a recombinant mammalian cell according to claim 12 to said patient.

* * * * *